US012583885B2

(12) United States Patent
Manzer et al.

(10) Patent No.: US 12,583,885 B2
(45) Date of Patent: Mar. 24, 2026

(54) COMPOSITIONS OF HYBRID SUPPORTED LIPID BILAYERS AND METHODS FOR PRODUCING

(71) Applicant: Cornell University, Ithaca, NY (US)

(72) Inventors: Zachary Manzer, Ithaca, NY (US); Surajit Ghosh, Ithaca, NY (US); Susan Daniel, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 158 days.

(21) Appl. No.: 17/526,327

(22) Filed: Nov. 15, 2021

(65) Prior Publication Data

US 2022/0153778 A1     May 19, 2022

Related U.S. Application Data

(60) Provisional application No. 63/113,333, filed on Nov. 13, 2020.

(51) Int. Cl.
| | |
|---|---|
| *C07K 1/00* | (2006.01) |
| *C07K 1/08* | (2006.01) |
| *C07K 1/107* | (2006.01) |
| *C07K 17/02* | (2006.01) |
| *C08F 8/32* | (2006.01) |

(52) U.S. Cl.
CPC ............ *C07K 1/082* (2013.01); *C07K 1/1077* (2013.01); *C07K 17/02* (2013.01); *C08F 8/32* (2013.01)

(58) Field of Classification Search
CPC ...... C07K 1/082; C07K 1/1077; C07K 17/02; C08F 8/32
See application file for complete search history.

(56) References Cited

U.S. PATENT DOCUMENTS

2006/0258587 A1* 11/2006 Kocer ................... A61K 9/127
530/424

OTHER PUBLICATIONS

Jacobs et al. (PNAS, Mar. 5, 2019, vol. 116, No. 10, pp. 4031-4036.*
Willes et al. Polymers. 2020, 12, 745.*
Fielder et al. Cell. Mol. Life Sci. (2010) 67:1779-1798.*
Jacobs et al., "Diblock copolymers enhance folding of a mechanosensitive membrane protein during cell-free expression," Proc Natl Acad Sci USA. 116(10):4031-4036 (including supplementary information) (23 pages) (Feb. 2019).
Yang et al., "Protein Interactions with Poly(ethylene glycol) Self-Assembled Monolayers on Glass Substrates: Diffusion and Adsorption," Langmuir. 15(24):8405-8411 (Sep. 1999).

* cited by examiner

*Primary Examiner* — Jeanette M Lieb
(74) *Attorney, Agent, or Firm* — MARSHALL, GERSTEIN & BORUN LLP

(57) ABSTRACT

The invention relates to hybrid supported lipid bilayer (HSLB) including a phospholipid; a copolymer; and a membrane protein, wherein the membrane protein is functional, properly oriented within the lipid bilayer, and mobile within the lipid bilayer.

20 Claims, 20 Drawing Sheets

A. <u>0 mol% Polymer</u>
(a) FRAP Images (b) Line scan across the beaching spot          (c) Recovery Curve B. <u>15 mol% Polymer</u>
(a) FRAP Images (b) Line scan across the beaching spot (c) Recovery Curve C. 25 mol% Polymer
 (a) FRAP Images (b) Line scan across the beaching spot (c) Recovery Curve D. 35 mol% Polymer
(a) FRAP Images (b) Line scan across the beaching spot (c) Recovery Curve E. <u>50 mol% Polymer</u>
(a) FRAP Images (b) Line scan across the beaching spot (c) Recovery Curve F. 100 mol% Polymer
(a) FRAP Images (b) Line scan across the beaching spot (c) Recovery Curve

1

COMPOSITIONS OF HYBRID SUPPORTED LIPID BILAYERS AND METHODS FOR PRODUCING

CROSS-REFERENCE TO RELATED APPLICATION

This application claims benefit of U.S. Provisional Application No. 63/113,333 filed Nov. 13, 2020, which is hereby incorporated by reference in its entirety.

STATEMENT REGARDING FEDERAL FUNDING

This invention was made with government support under contract No. MCB-1935370 awarded by the National Science Foundation. The government has certain rights in the invention.

BACKGROUND OF THE INVENTION

The assembly of cellular mimetic membranes containing functional, oriented membrane proteins remains a long-standing goal of biologists, biophysicists, and engineers alike. This is because the ability to harness membrane proteins, with their exquisite sensitivity, precise molecular recognition, and specific transport capabilities, and assemble them into material interfaces has significant potential for the structural and functional assessment of membrane proteins as well as biotechnological and pharmaceutical applications. Materials made from membrane components have led to the design of biosensors, gene sequencers, and platforms to screen pharmacological drug candidates (Peetla et al., Mol. Pharm. 2010, 7 (6), 2334-2348; Misawa et al., J. R. Soc. Interface 2018, 15 (141), 20170952). Nowhere has this goal been more closely achieved than with Supported Lipid Bilayers (SLBs), planar lipid membranes that can interface with electronic (Liu et al., Langmuir 2020, 36 (26), 7325-7331; Pappa et al., ACS Nano 2020), optical (Shi et al., Anal. Chem. 2008, 80 (15), 6078-6084; Costello et al., Biomaterials 2013, 34 (32), 7895-7904), and spectroscopic systems (Richter et al., Biophys. J. 2005, 88 (5), 3422-3433; Lee et al., Chem. Rev. 2018, 118 (11), 5392-5487) to enable biological activity to be detected and transduced into measurable readouts.

SLBs can be readily assembled on solid surfaces by a number of convenient methods from liposome fusion (Richter et al., Langmuir 2006, 22 (8), 3497-350), Langmuir-Blodgett-Schaeffer transfer (Tamm et al., Biophys. J. 1985, 47 (1), 105-11), or solvent-assisted lipid bilayer (SALB) formation (Jackman et al., Langmuir 2020, 36, 1387-1400). Due to their planar geometry, SLBs are compatible with various surface sensitive characterization and analytical tools including quartz crystal microbalance with dissipation (QCM-D) (Richter et al., Biophys. J. 2005, 88 (5), 3422-3433; Cho et al., Nat. Protoc. 2010, 5 (6), 1096-1106), surface plasmon resonance (SPR), atomic force microscopy (AFM) (Lee et al., Chem. Rev. 2018, 118 (11), 5392-5487; Richter et al., Biophys. J. 2005, 88 (5), 3422-3433), electrochemical impedance spectroscopy (EIS) (Liu et al., Langmuir 2020, 36 (26), 7325-7331; Pappa et al., ACS Nano 2020), and fluorescence microscopy (Glazier et al., Biochim. Biophys. Acta—Biomembr. 2017, 1859 (9), 1465-1482). The stability of SLBs (owing to the solid support) and their compatibility with various analytical techniques make them popular and convenient model biomembrane surfaces (Castellana et al., Surf. Sci. Rep. 2006, 61 (10), 429-444; Hsia et al., Anal. Methods 2015, 7 (17), 7076-7094).

Incorporating functional membrane proteins that are both oriented and mobile into SLBs, however, has been a significant challenge that has limited the full application of SLBs as biosensors or biophysical platforms. Typically, membrane proteins are integrated into SLBs using detergent-mediated reconstitution processes to first assemble proteoliposomes followed by liposomal rupture to form an SLB. This type of approach has limitations, because either the proteoliposomes are too stiff to rupture or the vesicles are incompatible with the surface to foster rupture. Furthermore, the detergents used to assemble proteoliposomes will inevitably end up in the resulting SLB, changing the membrane composition and properties in unexpected ways. An alternative method is to extract cell blebs from the plasma membrane surfaces and induce their rupture into a planar bilayer. This method, too, has drawbacks, especially for applications where the complexity of plasma membrane would confound investigations into a single protein or where the properties of the membrane need to be tightly controlled. Thus, there is a need for a new approach to integrate folded transmembrane proteins into supported bilayers of controlled compositions, while maintaining the salient features of lipid and protein mobility and protein orientation in the membrane.

SUMMARY OF THE INVENTION

In one aspect, the invention features a hybrid supported lipid bilayer (HSLB) including a phospholipid; a copolymer; and a membrane protein, wherein the membrane protein is functional, properly oriented within the lipid bilayer, and mobile within the lipid bilayer.

In embodiments, the phospholipid includes one or more phospholipids selected from the group consisting of 1,2-dioleoyl-sn-glycero-3-phosphocholine (DOPC) and poly (ethylene oxide)-b-polybutadiene ($PEO_{14}$-b-$PBD_{22}$).

In embodiments, the copolymer includes a diblock copolymer.

In embodiments, the copolymer includes poly(ethylene oxide)-b-poly(butadiene) (PEO-b-PBD).

In embodiments, the HSLB includes at least 25, 30, 35, 40, 45, or 50 mol % of copolymer.

In embodiments, the HSLB includes between 25-35 mol % of copolymer.

In embodiments, the membrane protein includes an integral membrane protein.

In embodiments, the membrane protein includes mechanosensitive channel of large conductance (MscL).

In embodiments, the membrane protein is properly oriented within the lipid bilayer when it is oriented in a native physiological orientation.

In embodiments, the HSLB includes a plurality of copies of the membrane protein and wherein at least 90% of the plurality of copies of the membrane protein have a native physiological orientation.

In embodiments, the HSLB includes a plurality of copies of the membrane protein and wherein at least 95% of the plurality of copies of the membrane protein have a native physiological orientation.

In another aspect, the invention features a method of preparing HSLB according to any of the aforementioned embodiments. Such methods include: preparing a hybrid vesicle including phospholipids and copolymers; and expressing a membrane protein with a cell-free expression system, wherein the membrane protein is co-translationally inserted into the hybrid vesicle; and fusing the hybrid vesicle to form a HSLB.

In still another aspect, the invention features a method of preparing the HSLB according to any of the aforementioned embodiments. Such methods include: forming a HSLB including a phospholipid and a copolymer; and expressing a membrane protein with a cell-free expression system, wherein the membrane protein is co-translationally inserted into the HSLB.

Other features and advantages of the invention will be apparent from the following Detailed Description and the Claims.

BRIEF DESCRIPTION OF THE DRAWINGS

For a more complete understanding of the principles disclosed herein, and the advantages thereof, reference is now made to the following descriptions taken in conjunction with the accompanying drawings.

variation of diameter and (c) zeta potential of vesicles composed of DOPC and PEO-b-PBD using TR-DHPE as fluorophore.

Figure 6:
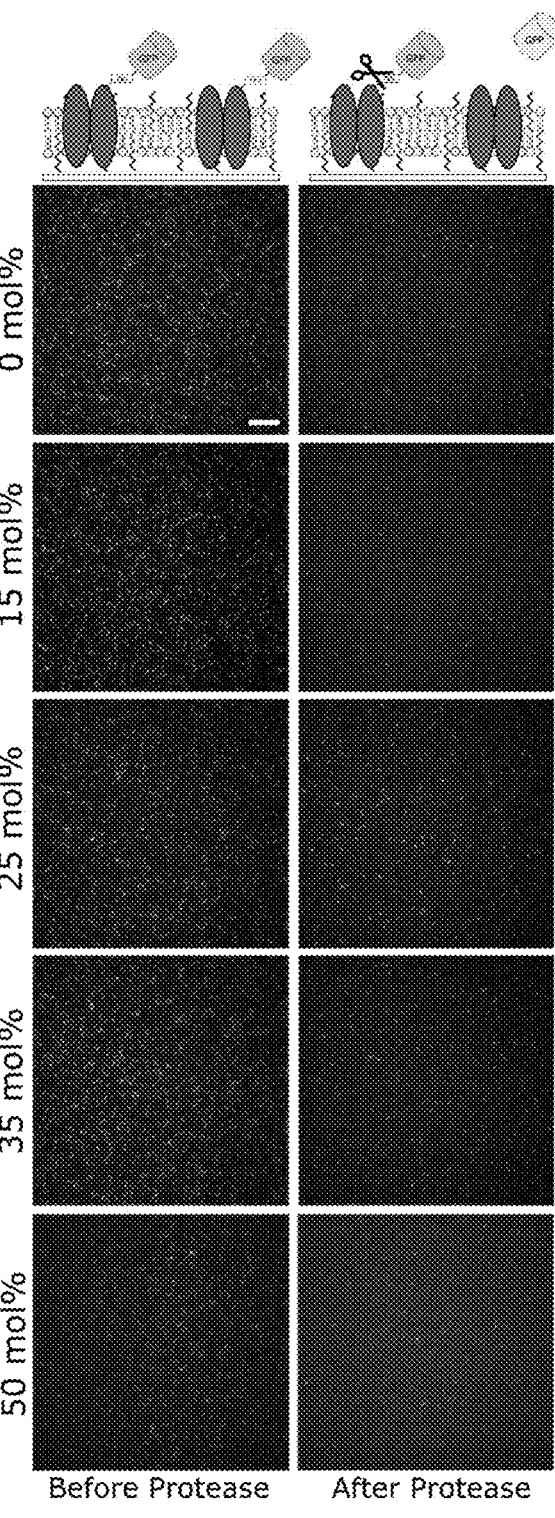

FIG. 6 shows a protease orientation assay for HSLBs formed by vesicle fusion. Protein orientation assay of HSLBs formed by vesicle fusion of proteoliposomes for HSLBs from 0 mol % to 35 mol % copolymer. GFP exposed to the top of the HSLB will be cleaved upon treatment with TEV protease. Scale bar 5 μm.

Figure 7:
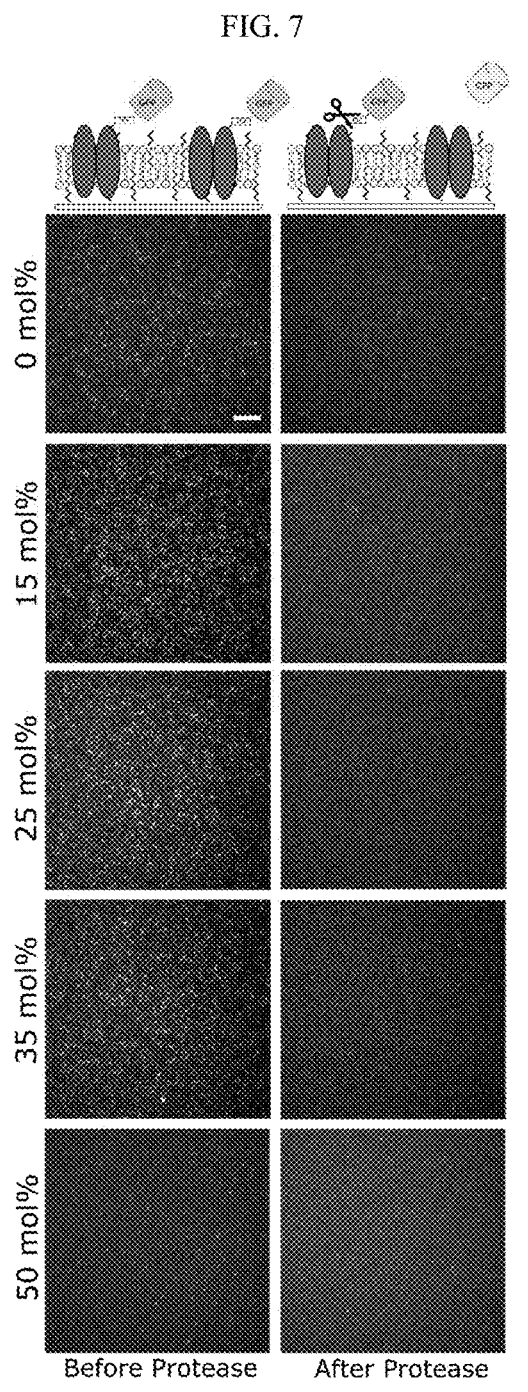

FIG. 7 shows a protease orientation assay for HSLBs formed by direct expression. Protein orientation assay for HSLBs formed by direct translation of protein into pre-formed HSLBs from 0 mol % to 35 mol % copolymer. GFP exposed to the top of the HSLB will be cleaved upon treatment with TEV protease. Scale bar 5 μm.

Figure 8:
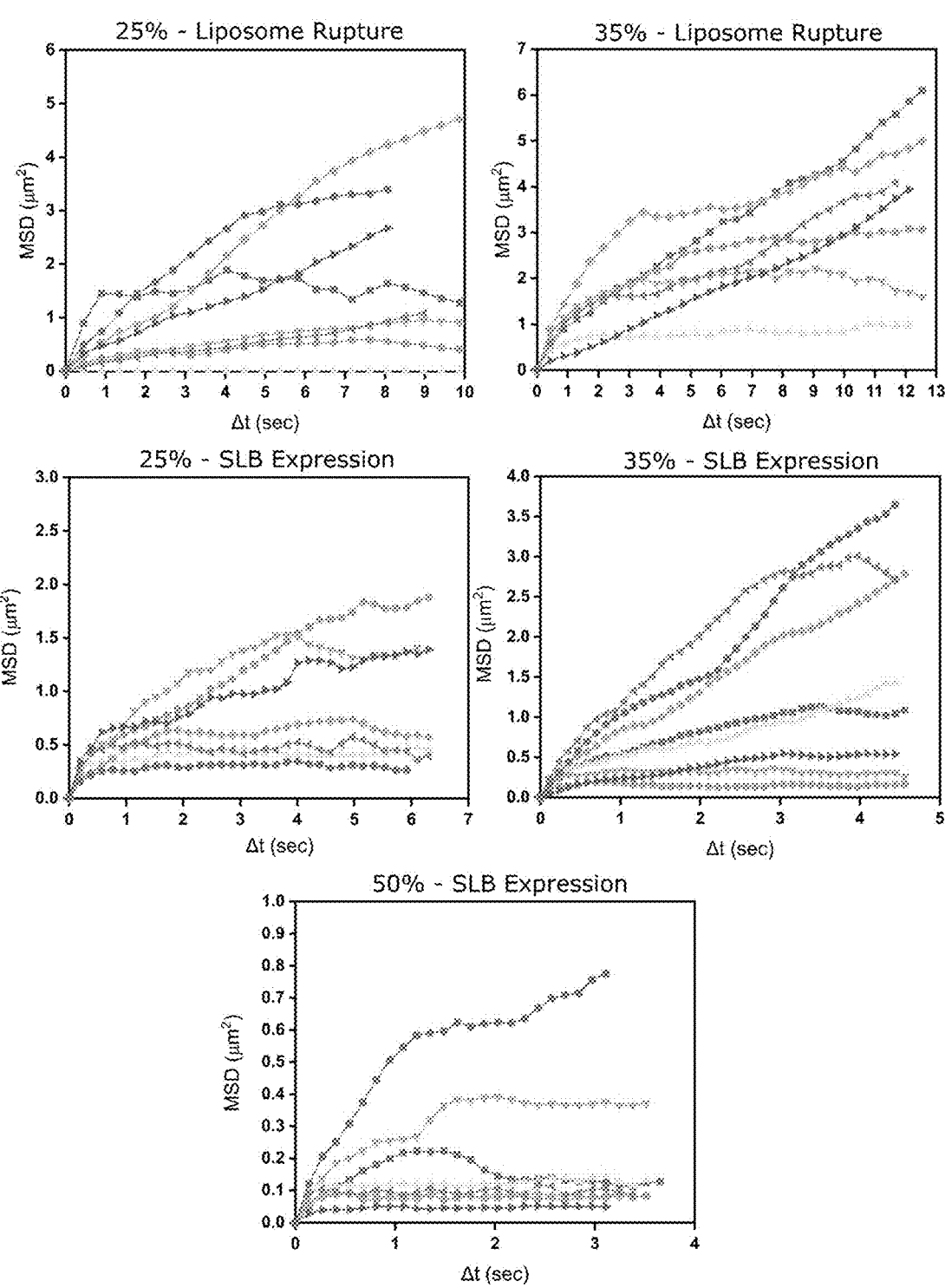

FIG. 8 shows a mean square displacement plots for mobile proteins in HSLBs. Representative mean square displacement (MSD) plots for each HSLB that was found to have mobile MscL-GFP, formed by the vesicle fusion method or direct expression into a preformed HSLB. Each case shows similar initial behavior and then exhibits behavior indicating confinement.

Figure 9:
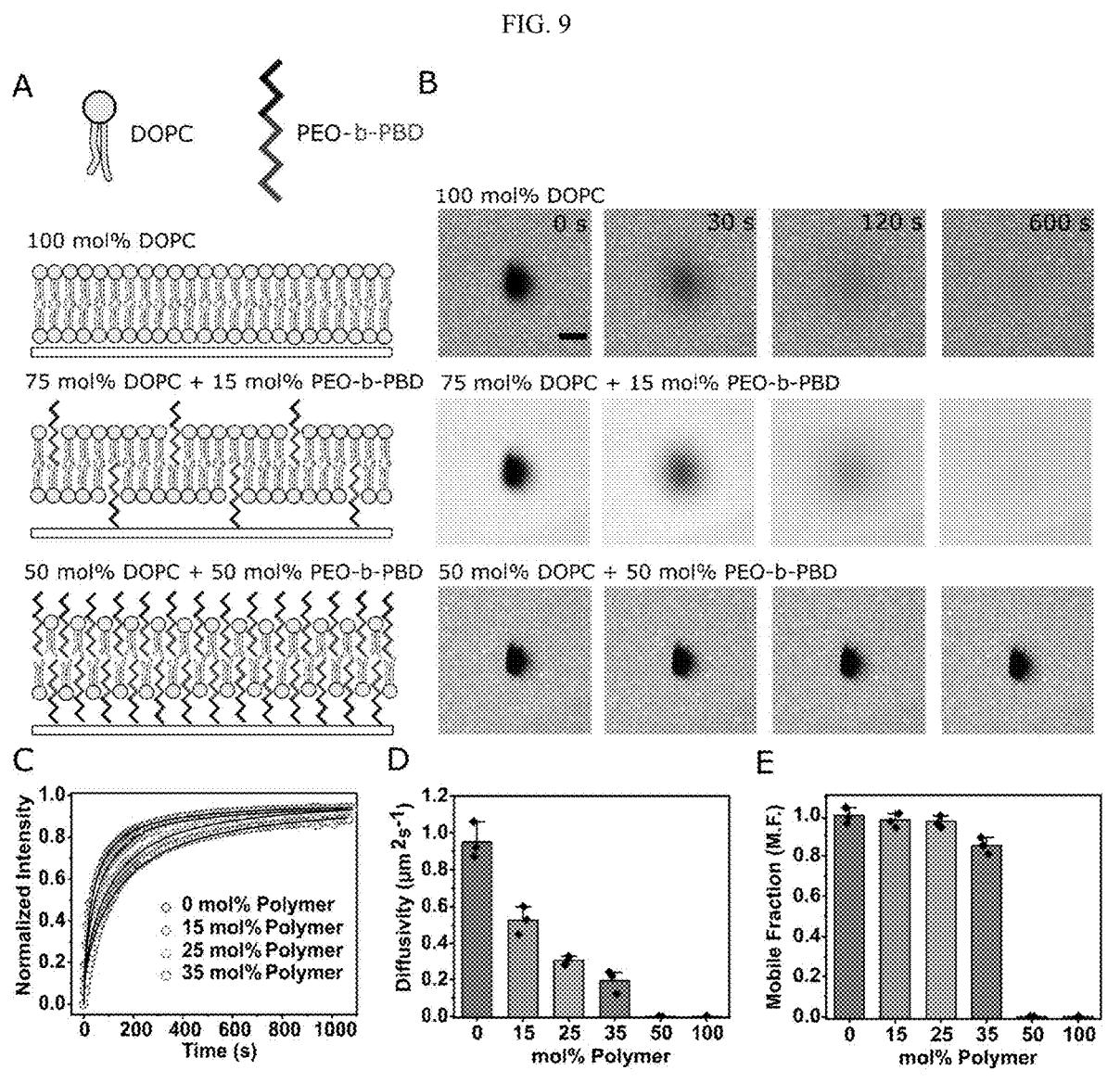

FIG. 9 shows HSLBs have two-dimensional fluidity. Characterization of hybrid SLB formation using DOPC and PEO-b-PBD containing vesicles. (A) Schematic representation of supported lipid bilayer (SLB) using DOPC and PEO-b-PBD on glass support. (B) FRAP images of SLB formed by fusion of vesicles (scale bar 20 μm). (C) The recovery of photobleaching spot intensity of FRAP images with time, (D) variation of diffusion coefficient, and (E) mobile fraction.

Figure 10:
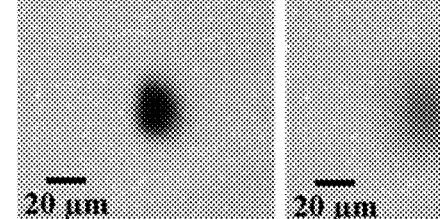
Figure 10:
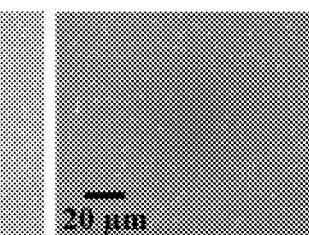
Figure 10:
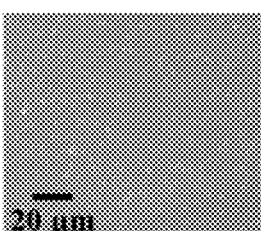
Figure 10:
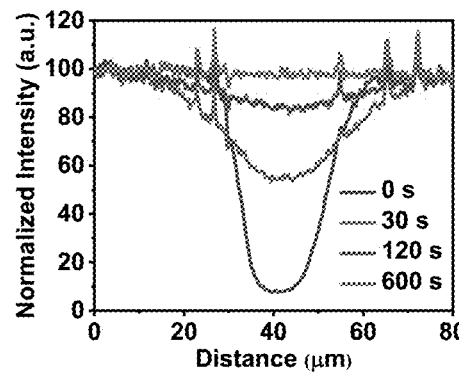
Figure 10:
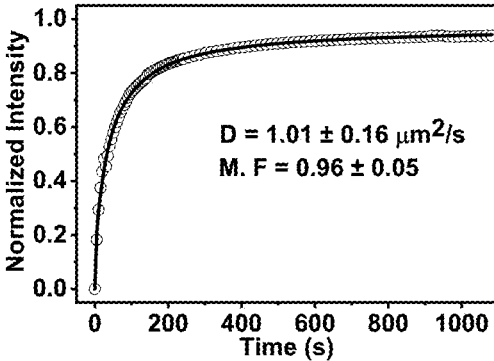
Figure 10:
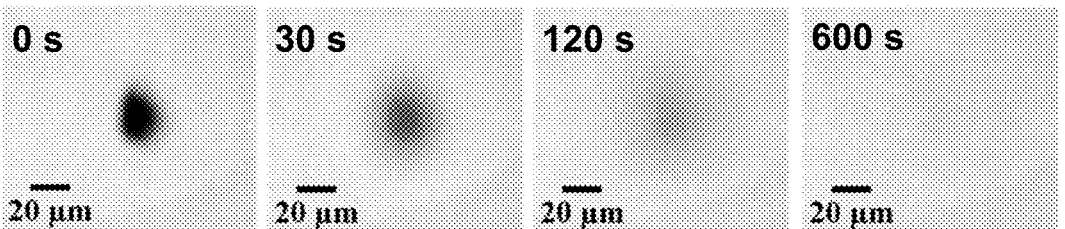
Figure 10:
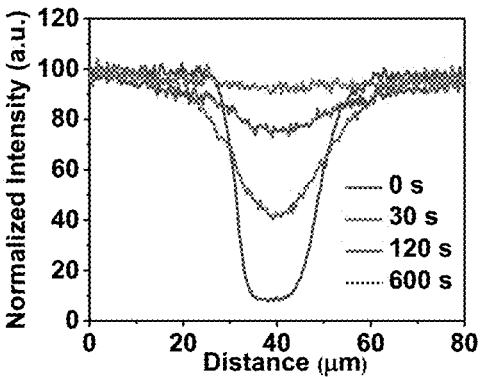
Figure 10:
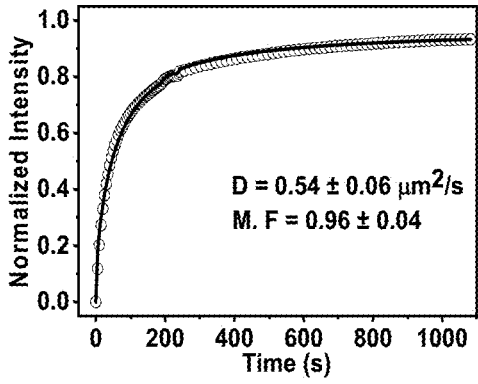
Figure 10:
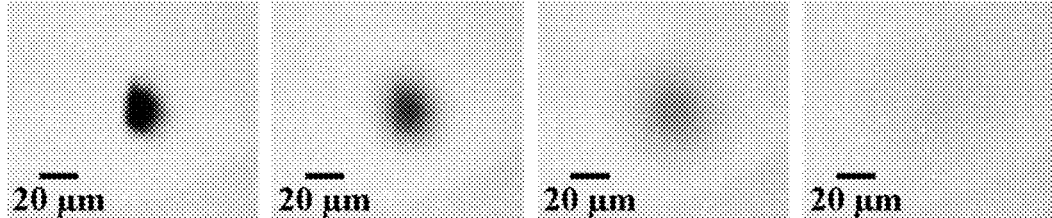
Figure 10:
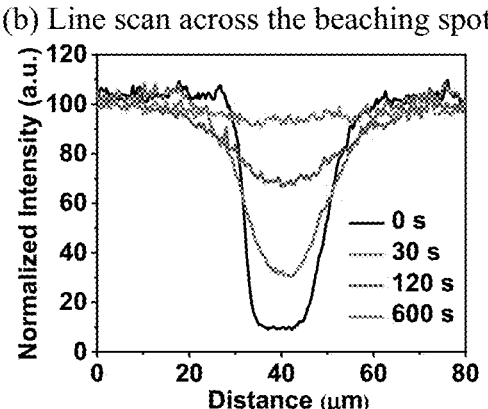
Figure 10:
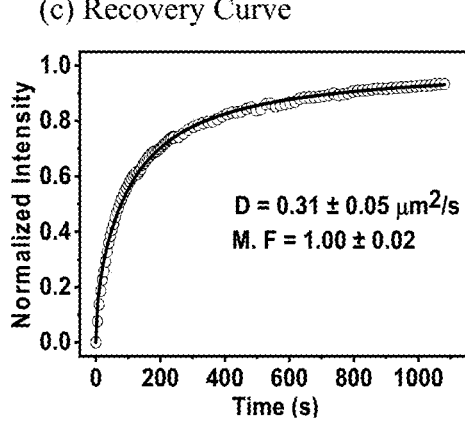
Figure 10:
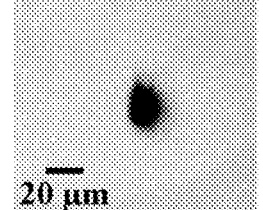
Figure 10:
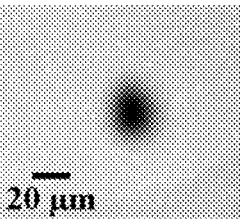
Figure 10:
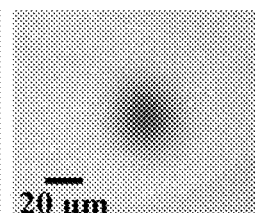
Figure 10:
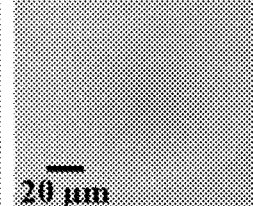
Figure 10:
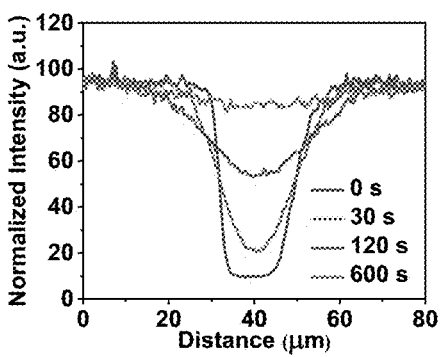
Figure 10:
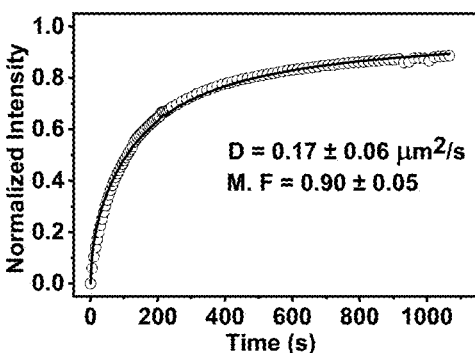
Figure 10:
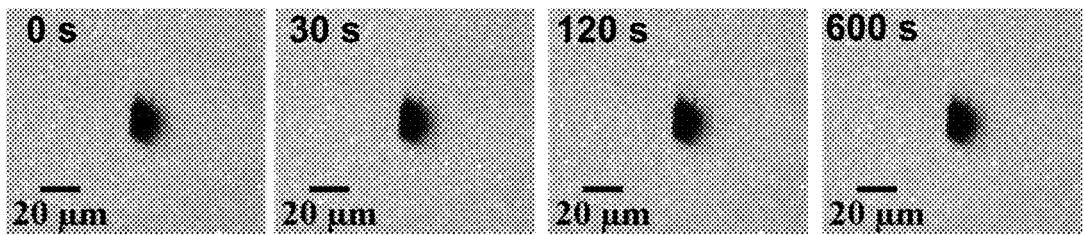
Figure 10:
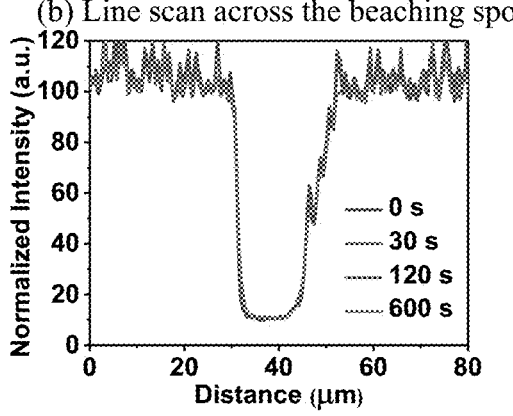
Figure 10:
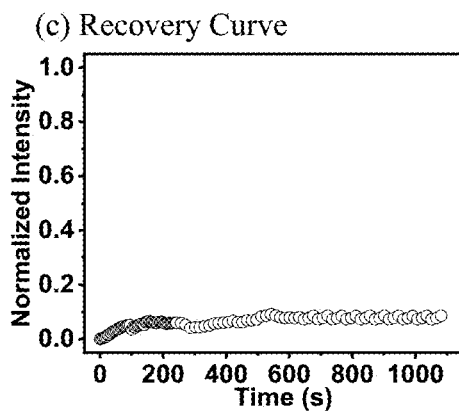
Figure 10:
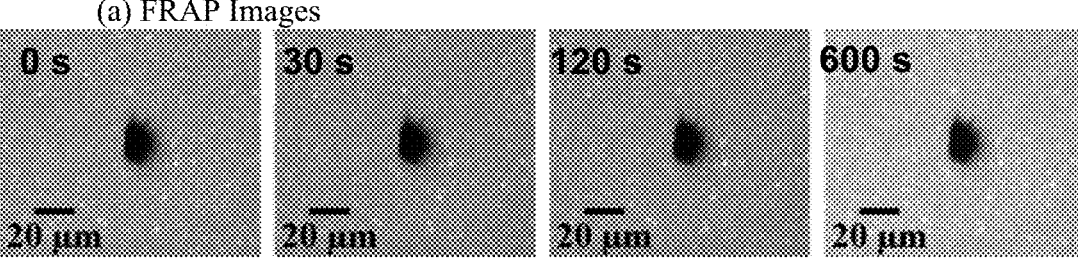
Figure 10:
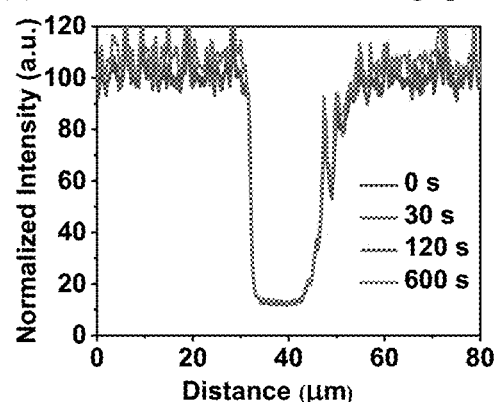
Figure 10:
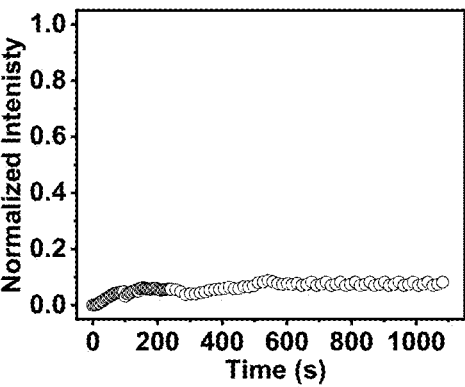

FIG. 10 shows HSLBs have two-dimensional fluidity. A. 0 mol % polymer. (a) FRAP images, (b) line scans across the photobleaching spot and (c) recovery curve to show the intensity recovery over time in various liposome compositions using TR-DHPE as fluorophore. B. 15 mol % polymer. (a) FRAP images, (b) line scans across the photobleaching spot and (c) recovery curve to show the intensity recovery over time in various liposome compositions using TR-DHPE as fluorophore. C. 25 mol % polymer. (a) FRAP images, (b) line scans across the photobleaching spot and (c) recovery curve to show the intensity recovery over time in various liposome compositions using TR-DHPE as fluorophore. D. 35 mol % polymer. (a) FRAP images, (b) line scans across the photobleaching spot and (c) recovery curve to show the intensity recovery over time in various liposome compositions using TR-DHPE as fluorophore. E. 50 mol % polymer. (a) FRAP images, (b) line scans across the photobleaching spot and (c) recovery curve to show the intensity recovery over time in various liposome compositions using TR-DHPE as fluorophore. F. 100 mol % polymer. (a) FRAP images, (b) line scans across the photobleaching spot and (c) recovery curve to show the intensity recovery over time in various liposome compositions using TR-DHPE as fluorophore.

Figure 11:
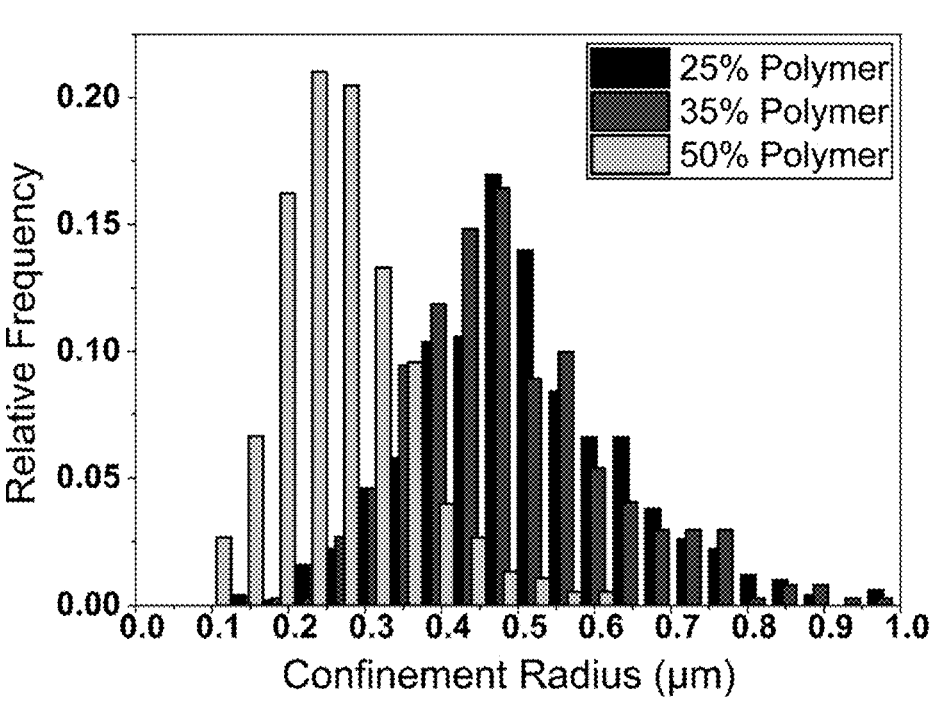

FIG. 11 shows the calculated confinement radius for mobile proteins. Calculated confinement radius of diffusive MscL-GFP for 25-50 mol % diblock copolymer formed by direct expression into a preformed HSLB. The confinement radius for 25 and 35 mol % diblock copolymer exhibits similar behavior. HSLBs containing 50 mol % diblock copolymer have proteins with a confinement radius nearly half of the other samples.

Figure 12:
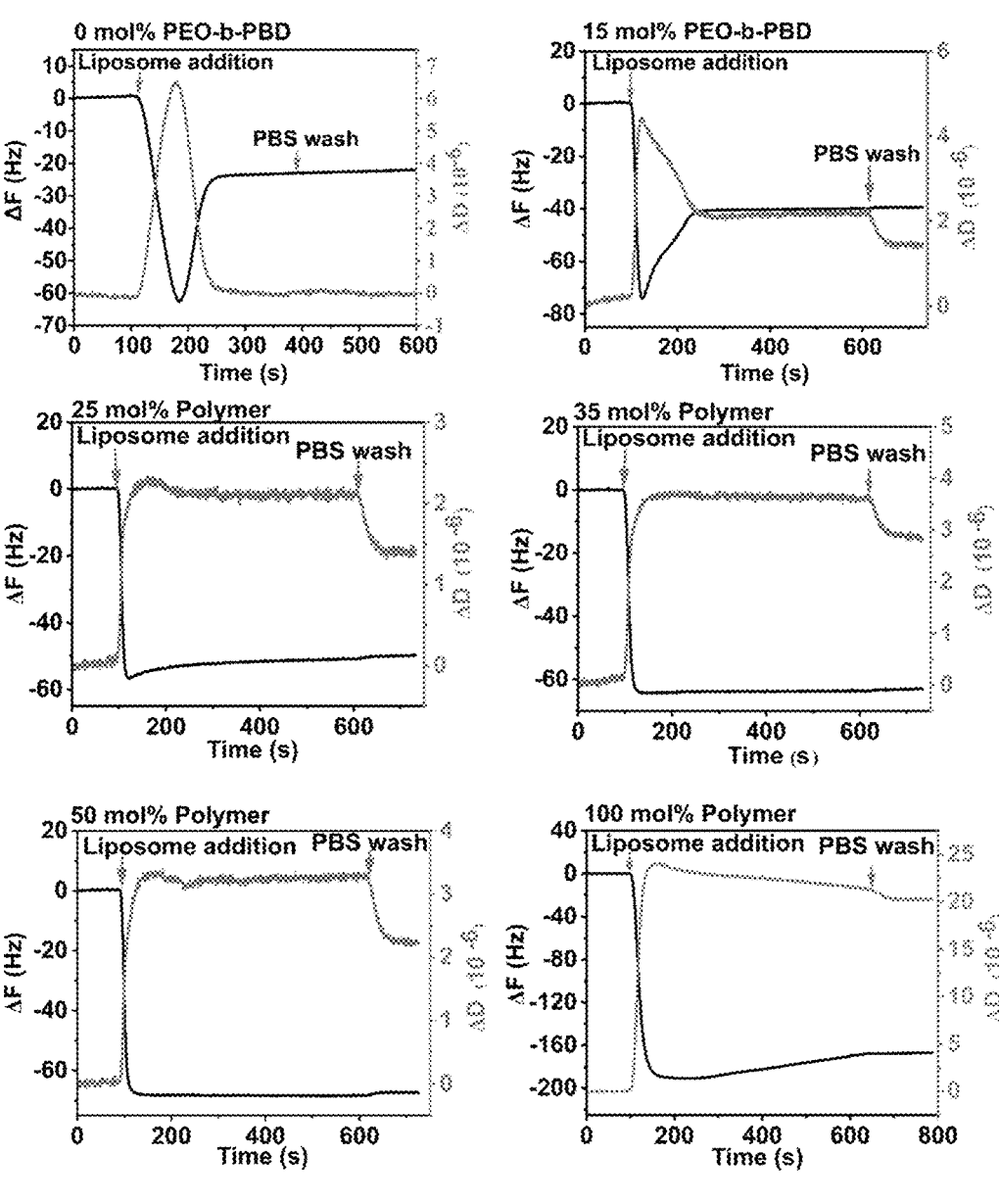

FIG. 12 shows a QCM-D analysis; frequency and dissipation change as a function of time. QCM-D frequency and dissipation change as a function of time for vesicle adsorption and supported hybrid bilayer containing DOPC and PBD-b-PEO with mol percentage.

Figure 13:
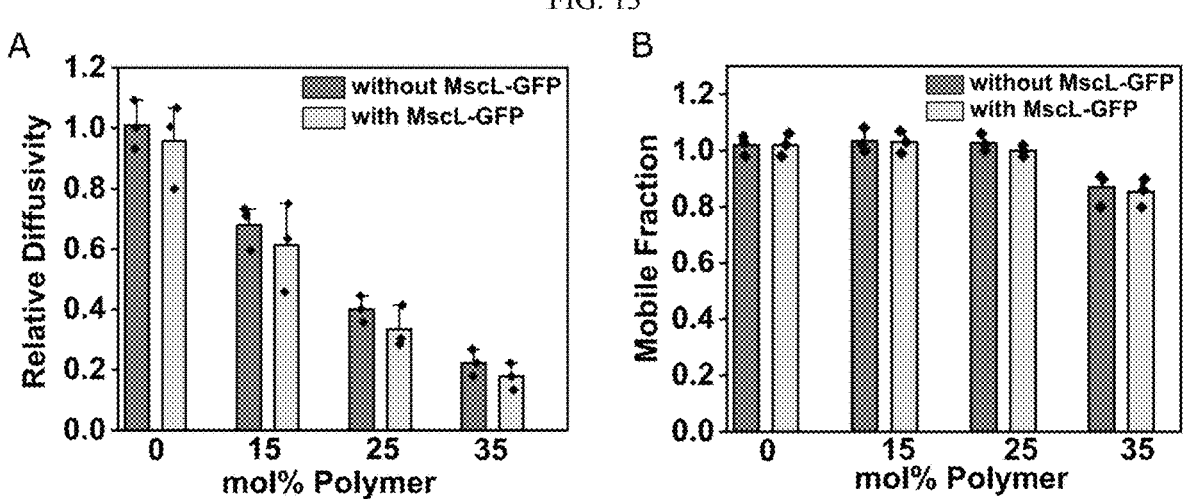

FIG. 13 shows incorporation of MscL-GFP does not affect lipid diffusivity or mobile fraction. Incorporation of MscL-GFP does not affect lipid diffusivity or mobile fraction. (A) HSLBs with and without MscL-GFP incorporated using cell-free protein synthesis were labelled with R18 to measure lipid diffusivity and mobile fraction. We see the same trend as we observed previously. (B) Overall lipid mobile fraction remains high after protein incorporation.

Figure 14:
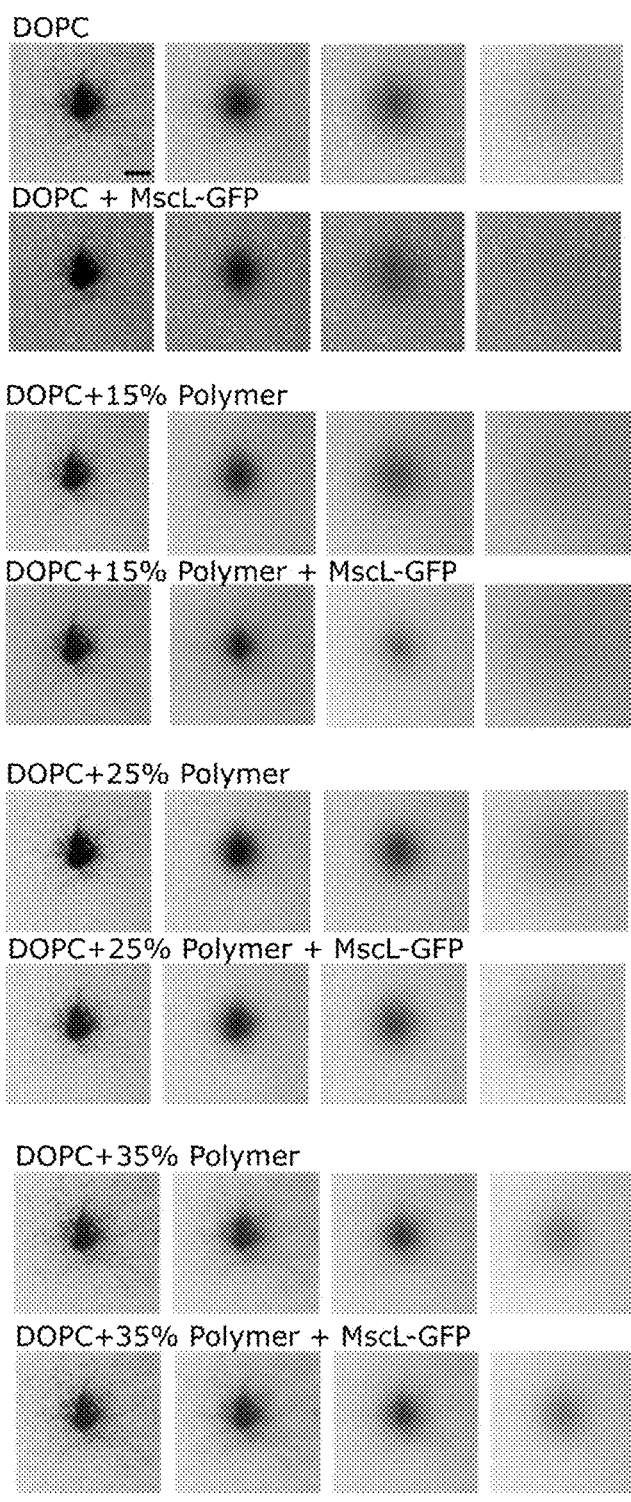

FIG. 14 shows FRAP images of HSLBs with and without expressed MscL-GFP. FRAP Images of HSLBs containing from 0 mol % to 35 mol % polymer, with and without expressed MscL-GFP. The incorporation of protein into the HSLB did not significantly affect lipid recovery time or overall lipid mobile fraction. Scale bar 20 μm.

Figures 15, 16:
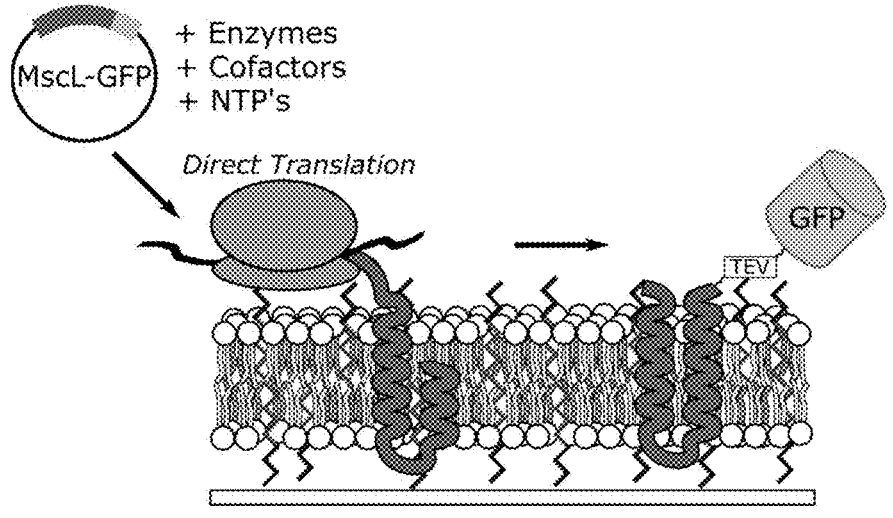

FIG. 15 shows a schematic of cell free co-translational insertion of membrane protein to form HSLB.

FIG. 16 shows a subunit photobleaching experiment of MscL-GFP in 25% diblock copolymer HSLB. (A) Representative intensity-time trace of the photobleaching steps observed for MscL-GFP. Five photo-bleaching steps are denoted by arrow marks. (B) Histogram of the number of photobleaching steps from the intensity-time trace and fitted to binomial distribution for a total of n=350 spots.

DETAILED DESCRIPTION

Below we present the use of cell-free protein synthesis (CFPS) to incorporate a membrane protein into a HSLB using two complementary approaches that offer flexibility in reaction conditions and desired surfaces depending on the intended application. We observe that both methods result in oriented proteins and that these proteins are mobile in HSLBs above a certain diblock copolymer concentration, overcoming significant limitations of previous methods of protein-integrated SLBs. The ability to create a HSLB with proteins expressed in a cell-free manner unlocks a wide variety of applications from basic biophysics to biotechnology that are otherwise difficult to attain by traditional methods. In particular, we report using cell-free expression systems for the co-translational insertion of membrane proteins into hybrid supported lipid bilayers (HSLBs) containing phospholipids and diblock copolymers (FIG. 15). We use cell free expression techniques and a model protein, the mechanosensitive channel of large conductance (MscL), to demonstrate two routes to integrate a channel protein into a HSLB. We show that HSLBs can be assembled with integrated membrane proteins by either co-translational integration of protein into hybrid vesicles, followed by fusion of these proteoliposomes to form a HSLB, or preformation of a HSLB followed by the cell-free synthesis of the protein directly into the HSLB. Both approaches lead to the assembly of HSLBs with oriented proteins. Notably, we find, using single particle analysis, that the presence of diblock copolymers facilitates membrane protein mobility in the HSLBs, a critical feature that has been difficult to achieve in pure lipid SLBs. The approach presented here to integrate membrane proteins directly into preformed HSLBs using cell-free co-translational insertion is an important step toward enabling many biotechnology applications including biosensing, drug screening, and materials platforms requiring cell membrane-like interfaces that bring together the abiotic and biotic worlds.

Experimental:

Materials:

1,2-dioleoyl-sn-glycero-3-phosphocholine (DOPC) and poly(ethylene oxide)-b-polybutadiene ($PEO_{14}$-b-$PBD_{22}$, 1800 kDa) were obtained from Avanti Polar Lipids (Alabaster, AL, USA) and Polymer Source Inc (Montreal, Quebec, Canada), respectively. Texas Red 1,2-dihexadecanoyl-sn-glycero-3-phosphoethanolamine, triethylammonium salt (TR-DHPE) was obtained from Thermo Fisher Scientific. Phosphate buffered saline (PBS), and Sepharose 4B were obtained from Sigma-Aldrich (St. Louis, MO, USA). All chemicals were used without further purification.

Plasmid Information:

pET19b-EcMscL-mEGFP has been described previously (Jacobs et al., Proc. Natl. Acad. Sci. U.S.A 2019, 116 (10), 4031-4036)[22]. Briefly, the *E. coli* mechanosensitive channel of large conductance (EcMscL) is C-terminally fused to monomeric enhanced green fluorescent protein (mEGFP) under the T7 promoter for cell-free protein expression. A Tobacco Etch Virus (TEV) protease cleavage site is located between MscL and GFP to allow for post-expression GFP removal.

Small Unilamellar Vesicle Preparation:

Small unilamellar vesicles (SUVs) with varying mol % of DOPC and $PEO_{14}$-b-$PBD_{22}$ were prepared using thin-film hydration methods (Kamat et al., Adv. Funct. Mater. 2010, 20 (16), 2588-2596).[28] Briefly, required amounts of DOPC in $CHCl_3$ and $PEO_{14}$-b-$PBD_{22}$ in $CH_2Cl_2$ were mixed together in glass vials to achieve the desired mole percentage with a total amphiphile concentration of 5 mM for SLB formation and 26.09 mM for cell-free expression. Excess solvent was evaporated by rotation under a stream of nitrogen to form a lipid film. Films were further dried under vacuum for >4 h to remove trace amounts of solvent. Finally, the films were rehydrated with 300 mOsm PBS (SUVs used for cell-free expression were rehydrated in water instead of PBS) and incubated overnight at 60° C. The films were then vortexed for several seconds and extruded seven times through 100 nm Nucleopore polycarbonate membrane using an Avanti Mini Extruder (Avanti Polar Lipids, Birmingham, AL).

Characterization of Liposome Size and Surface Charge:

The hydrodynamic size (diameter) and surface charge (zeta potential) of the liposomes in 300 mOsm PBS were measured on a Malvern Instruments Zetasizer Nano-ZS instrument with a 4 mW He—Ne laser (λ=632 nm) and backscattered detector angle 173°. The results are summarized in FIG. 5.

Glass Slide Preparation:

Microscope cover glass (25×25 mm; No. 1.5; VWR) was cleaned by immersion in a solution containing 70% sulfuric acid ($H_2SO_4$) and 30% hydrogen peroxide ($H_2O_2$) for 10 m and then washed under deionized water (18.2 MΩ cm) for 30 m. Just prior to use, the glass slides were dried with a stream of nitrogen and used immediately to assemble supported lipid bilayers.

Supported Lipid Bilayer Formation:

Cleaned glass slides were used as solid surface for supported lipid bilayer formation. First, PDMS (polydimethylsiloxane, 10:1 elastomer: cross-linker mixture of Sylgard 184) wells (with diameter of ~1 cm) were attached to cleaned dried glass slide. Then, 80 μL of liposome solution with ~0.75 mM concentration was added into the well and incubated for 15-20 m. This minimum incubation time is needed for liposome absorption on the glass slide and subsequent rupture of vesicles to form a contiguous, planar supported lipid bilayer. After formation, the well was rinsed with PBS to remove excess unruptured liposomes.

Fluorescence Recovery after Photobleaching (FRAP) Measurements:

To verify the formation of fluid supported lipid bilayer on the glass surface, we monitored fluorescence recovery after photobleaching (FRAP) of fluorescently labelled phospholipids doped into the phospholipid and diblock containing hybrid bilayer films. ~1.0 mol % TR-DHPE was added to all liposome formulations for the FRAP experiments. The instrumental set up for FRAP measurement consists of an inverted Zeiss Axio Observer Z1 microscope with an α Plan-Apochromat 20× objective and 150 mW 561 nm optically pumped semiconductor laser (Coherent, Inc). After the formation of bilayer, the laser was used to bleach a ~20 μm diameter spot at the z-plane for 500 ms and then the recovery of the bleached spot's intensity was recorded over 30 min. After background subtraction and normalization for photobleaching effects, fluorescence intensity recovery data was fit to the 2-D diffusion equation following the method of Soumpasis et al.[29] The following equation was used to calculate the diffusion coefficient (D):

$$D = \frac{w^2}{t_{1/2}} \tag{1}$$

where w and $t_{1/2}$ represent radius of the photobleached spot and the time required to achieve half of the maximum recovery intensity, respectively.

Quartz Crystal Microbalance with Dissipation (QCM-D) Experiments:

QCM-D measurements were performed using Q-Sense E1 (Biolin Scientific, Sweden) instrument with silicon oxide-coated sensors (QSX 303, Q-Sense) to monitor liposome adsorption, their rupture process, and bilayer formation. All measurements were performed at ~25.0° C. with a flow rate of 100 μL/min by a peristaltic pump (Ismatec). First, the surface of QCM sensors were cleaned by oxygen plasma treatment for 1 min. The PBS buffer was then flowed through the QCM crystal and after obtaining a stable baseline, the liposome solution was injected. Supported lipid bilayer formation was monitored by recording the change of sensor resonance frequency (ΔF) and energy dissipation (ΔD) with time. The ΔF and ΔD values were observed at the odd overtones (1st-13th). In this article, the reported data were measured at 3rd overtone and analyzed using Q-tools software (v. 3.1.25.604, Nanoscience Instruments).

Quartz Crystal Microbalance with Dissipation (QCM-D) Monitors Bilayer Formation

The adsorption and rupture of hybrid vesicles on silica surfaces was monitored using QCM-D by measuring changes of resonance frequency (ΔF) and energy dissipation (ΔD). ΔF and ΔD provide information about the adsorbed lipid mass and viscoelastic properties of the adsorbed lipid layer on a silica surface and is a useful tool for monitoring the formation of SLBs from vesicles. The addition of DOPC liposomes to the QCM sensor showed characteristic behavior of supported bilayer formation: first, a substantial decrease in sensor frequency and increase in dissipation, owing to the adsorption of intact liposomes to the silica surface; followed by a sharp transition and increase in frequency and decrease in dissipation, which results from the rupture and formation of the planar bilayer film. The signal finally stabilizes with a ΔF=~25±2 Hz and ΔD=~0.2× $10^{-6}$ (FIG. 12), a well-known QCM-D response of SLB formation on silica surfaces (Richter et al., Biophys. J. 2005, 88 (5), 3422-3433).

Cell-Free Protein Synthesis (CFPS):

CFPS was performed using PURExpress In Vitro Protein Synthesis kit (E6800) from New England Biolabs, Inc. (Ipswich, MA). We followed the manufacturer's protocol for expression of proteins and supplemented in liposomes to replace $H_2O$ in the reaction mixture or conducted the reaction in the presence of SLBs. In each reaction, the total reaction volume was 30 μL containing PURExpress components, MscL-GFP plasmid (200 ng), and desired liposomes/SLBs.

During CFPS into liposomes, the concentration of liposomes was kept at ~10 mM and reaction was executed at 37° C. for ~2 hours. Finally, liposomes were purified by Sepharose CL-4B column using PBS as the eluent.

For CFPS into HSLB, we used ~0.8 mM liposomes in PBS to form HSLBs that were to be used for CFPS into HSLBs. After formation of HSLBs, samples were rinsed with PBS to remove unruptured liposomes and then with autoclaved Milli Q water to remove excess salts just prior to addition of the cell-free reaction mixture. CFPS reaction was executed at 37° C. for 30-40 min before rinsing the HSLBs with PBS to quench the reaction.

Rupture of MscL-GFP Expressed Vesicles and HSLB Formation:

To verify the rupture of proteoliposomes and HSLB formation from them, we labelled MscL-GFP expressed proteoliposomes with octadecyl rhodamine (R18, Molecular Probes), a membrane-intercalating fluorescent molecule. During labelling of proteoliposomes, 200 μL of MscL-GFP containing vesicle solution was incubated with 1 μL of 0.5 mM R18, (dissolved in ethanol), in a sonicating bath (VWR) for 15 min at 4° C. The labelled MscL-GFP expressed proteoliposomes in solution were incubated on a treated glass slide for 15 min to form HSLBs. This R18 labeling allowed visual observation of the state of proteoliposomes (i.e., they remain intact vesicles or rupture to form SLB) using a fluorescence microscope. We also did similar experiments with empty liposomes to compare the lipid diffusion between HSLBs with and without membrane proteins.

Cleavage Assay for Protein Orientation:

To determine the orientation of MscL-GFP in the HSLBs, TEV protease (New England Biolabs, Inc.) was used according to manufacturer's recommendations to cleave the GFP molecule from the membrane bound MscL. Samples were imaged using TIRF microscopy both before and after overnight incubation with the TEV protease to quantify the loss in fluorescence particles. Samples were covered during incubation to prevent photobleaching and cleaved GFP molecules were rinsed away using PBS before imaging. Punctate fluorescent particles were counted using ImageJ (Schneider et al., Nat. Methods 2012, 9 (7), 671-675).

Characterization of Individual Membrane Protein Motion:

To monitor the mobility and orientation of MscL-GFP, supported lipid bilayers containing protein were imaged using total internal reflection fluorescence (TIRF) microscopy on an inverted Zeiss Axio Observer.Z1 microscope with an α Plan-Apochromat 100× objective. 561 nm solid-state laser was used to excite the GFP for tracking. A Laser TIRF 3 slider (Carl Zeiss, Inc.) was used to control incident angle to create evanescent wave of ~100 nm. A Semrock LF488-B-ZHE filter cube was used to filter excitation light and sent to the electron-multiplying CCD camera (ImageEM C9100-13, Hamamatsu). All images were analyzed using ImageJ (NIH) and Matlab (Mathworks).

Results and Discussion:

Cell-Free Expression Methods Enable Incorporation of Oriented Membrane Proteins into HSLBs We used a cell-free protein synthesis (CFPS) method to incorporate a transmembrane protein into HSLBs. CFPS utilizes either purified synthesis components (Shimizu et al., Nat. Biotechnol. 2001, 19 (8), 751-755) or cellular lysate (Jewett et al., Mol. Syst. Biol. 2008, 4 (220)) to synthesize proteins in-vitro from DNA of interest. This expression system does not rely on living cells and is easily amenable to direct modifications, such as adding membrane supports into the reaction environment. To provide an amphiphilic environment to support membrane protein incorporation, we chose to form HSLBs using 1,2-dioleoyl-sn-glycero-3-phosphocholine (DOPC) and the diblock copolymer poly(ethylene oxide)-b-poly(butadiene) (PEO-b-PBD) because these systems are well-characterized and have been shown to positively influence membrane protein expression by providing a tunable amphiphilic environment (Jacobs et al., Proc. Natl. Acad. Sci. U.S.A 2019, 116 (10), 4031-4036). Additionally, we hypothesized the hydrophilic PEO group on the diblock copolymer may not only affect the diffusion of lipids in plane but also provide additional space under the HSLB to promote protein mobility, similar to other polymers used to cushion SLBs (Diaz et al., Langmuir 2008, 24 (13), 6820-6826; Liu et al., Langmuir 2018, 34 (3), 1061-1072). We used two approaches, each of which makes use of the flexibility of different SLB formation methods to provide a wide breadth of potential applications that require the incorporation of membrane proteins. In the first approach, we used CFPS to express a transmembrane protein, MscL-GFP, into hybrid vesicles and used vesicle fusion to self-assemble a HSLB containing these transmembrane proteins. In the second approach, we used CFPS to demonstrate the co-translational insertion of transmembrane proteins directly into preformed HSLBs. We determined that proteins embedded in the HSLB by either approach resulted in a predominant protein orientation, and that the addition of diblock copolymer to HSLBs promoted protein mobility in these HSLBs independent of formation technique.

Figure 5:
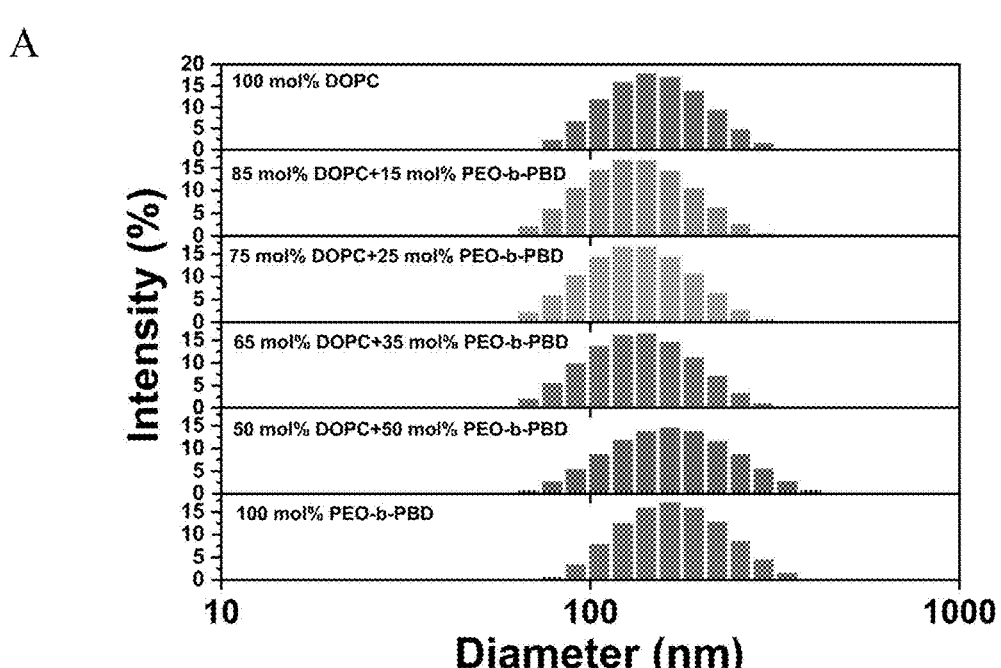
FIG. 5 shows a characterization of hybrid liposomes; Intensity-size distribution histogram, diameter and zeta potential of liposomes consisting of DOPC and PEO-b-PBD. (a) DLS Intensity-size distribution histogram, (b)
Figure 5:
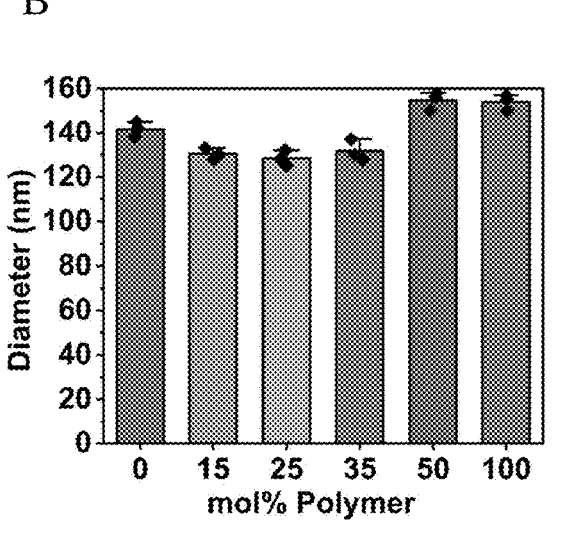
Figure 5:
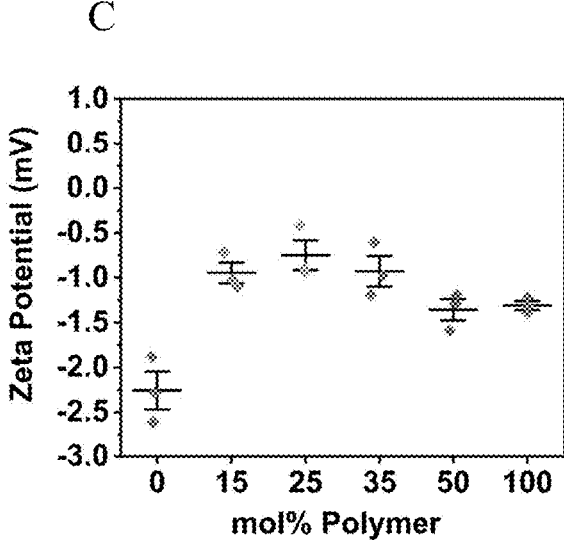

Characterization of Hybrid Vesicles and Supported Lipid Bilayers: Hybrid Liposomes have Consistent Size and Surface Charge Across Compositions To better understand the behavior of our HSLB system, we characterized the biophysical properties of the HSLB in the absence of protein. To understand the effect of blending lipids with synthetic amphiphiles on vesicle size and surface charge, we generated liposomes with different mol % of DOPC and PEO-b-PBD and performed dynamic light scattering studies (DLS). We found the hydrodynamic size distribution profiles of liposomes are monomodal in all compositions with a slight variation in average diameter and zeta potential (FIG. 5). These observations suggest that all hybrid liposomes have an almost identical diameter and zeta potential in all formulations and the resulting HSLBs formed from these vesicles are expected to likewise have similar surface charge regardless of the composition.

Approach 1: Proteoliposomes Made from Cell-Free Protein Expression Maintain Lipid Fluidity and Protein Orientation after Rupture to Form Supported Bilayers.

To test that proteoliposomes that incorporate co-translationally integrated membrane proteins could form a HSLB, we expressed a fluorescently-labelled transmembrane ion channel. The mechanosensitive channel of large conductance green fluorescent protein fusion (MscL-GFP) was expressed into liposomes containing various amounts of diblock copolymer and liposomes were ruptured post-expression to form bilayers. We analyzed membranes with polymer compositions of 0, 15, 25, 35, 50, and 100 mol % and assessed the capacity of hybrid membranes to form fluid bilayers and fluidize the embedded proteins. To confirm protein expression, we monitored an increase in fluorescence from MscL-GFP (Jacobs et al., Proc. Natl. Acad. Sci. U.S.A 2019, 116 (10), 4031-4036). GFP not only provides a straightforward way to monitor protein expression, but in this particular construct, the expression of GFP is a known reporter of proper protein folding (Waldo et al., Nat. Biotechnol. 1999, 17 (7), 691-695).

Figure 1:
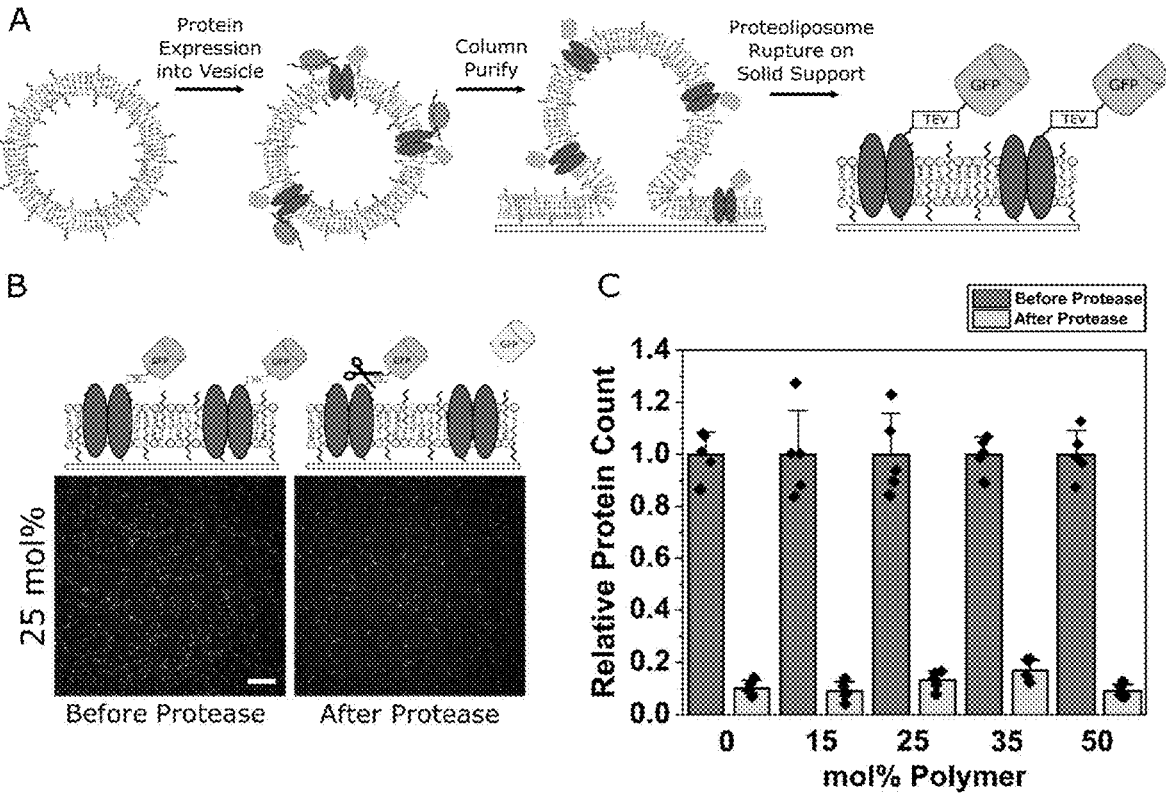
FIG. 1 shows the characterization of protein incorporation and orientation in HSLBs formed by the rupture of proteo-liposomes constructed using CFPS of MscL-GFP in the presence of hybrid vesicles. (A) Schematic representation of vesicle rupture process and resultant orientation of MscL-GFP. (B) Representative MscL-GFP signals in 25 mol % diblock copolymer HSLB before and after TEV protease treatment imaged using TIRF microscopy (scale bar 10 um). (C) Quantification of MscL-GFP cleavage for all compositions tested. The relative decrease in counted fluorescent punctate particles before and after TEV protease treatment indicates MscL-GFP in HSLBs was easily accessible (oriented away from the substrate).

We first wanted to determine protein orientation in our HSLBs. An illustration of the transition from vesicle to HSLB is shown in FIG. 1A. We used a fluorescence-based cleavage assay to determine the orientation of MscL-GFP after rupturing the hybrid vesicles containing cell-free expressed protein. MscL is expressed as a fusion protein with GFP connected by a TEV cleavage sequence, which can be cleaved by TEV protease. If the protein inserts from the external surface of the membrane, GFP is expected to be oriented towards the outside of the liposomes in solution. If the vesicles rupture on the solid support like "parachutes" with the outside leaflet facing up and the inside facing the support, the GFP should be oriented on the upper leaflet of the HSLB, facing the bulk solution. If this is the case where GFP is outward facing, upon TEV treatment, GFP will be cleaved and diffuse away from the HSLB into the bulk solution. If GFP is oriented facing the support, the TEV recognition sequence will be inaccessible to the enzyme and GFP should remain located there after treatment.

We used TIRF microscopy of GFP to determine protein orientation on our HSLBs using this TEV cleavage assay. The cleavage of the available fluorescent domain, i.e. GFP, by TEV protease resulted in the loss of fluorescent signal in HSLBs after all cleaved GFP portions were rinsed away, as depicted for 25 mol % diblock copolymer in FIG. 1B. Images for all compositions tested are shown in FIG. 6. All punctate fluorescent particles were counted before and after TEV treatment to quantify the change, as seen in FIG. 1C We observed that nearly 90% of expressed GFP is cleaved by the protease treatment and MscL-GFP, therefore, exhibits a predominantly unidirectional "upward" orientation in HSLBs. We hypothesize that the few particles that remain are likely due to unruptured liposomes on the surface of the glass or from protein that might have folded in a way that the TEV cleavage site is not easily accessible against the glass support, both of which represent less than roughly 10% of all synthesized proteins. The spontaneous rupture of hybrid vesicles containing cell-free expressed transmembrane proteins demonstrates the integration of membrane proteins into a HSLB with conserved orientation. This first approach relies on the self-assembly of HSLBs from the liposome fusion method, which provides advantages when wanting to coat a surface of complicated or inaccessible geometries with proteinaceous HSLBs, for example, the interior of microfluidic channels. These observations also suggest that the presence of the diblock copolymer does not change the resultant orientation of MscL-GFP after bilayer formation.

Approach 2: Direct Translation of Proteins into Hybrid Supported Lipid Bilayers Serves as Another Technique to Form Protein-Containing Supported Bilayers with Controlled Protein Orientation.

Figure 2:
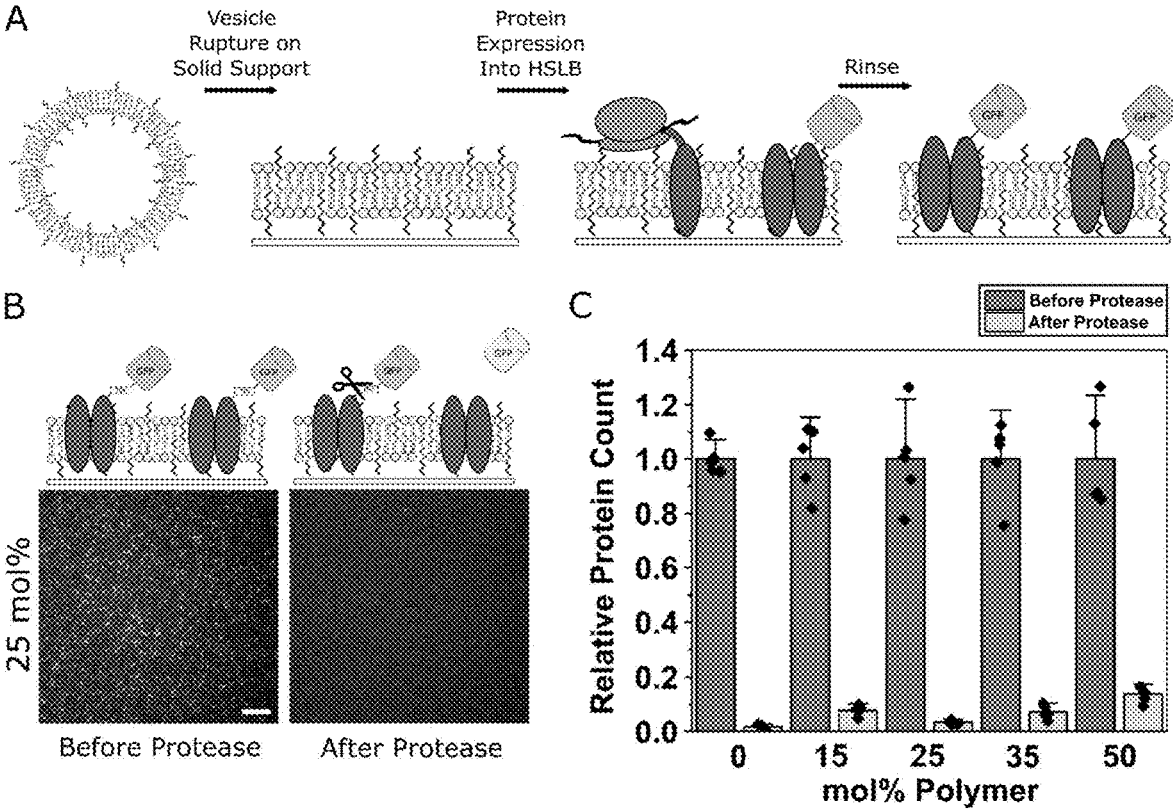
FIG. 2 shows the characterization of protein incorporation and orientation in HSLBs formed by the direct CFPS of MscL-GFP into a preformed HSLB (A) Schematic of cell-free co-translational insertion of protein directly into a preformed HSLB and its resultant orientation. (B) Representative MscL-GFP signals in a 25 mol % polymer HSLB before and after TEV protease treatment (scale bar 10 μm). (C) Quantification of MscL-GFP protein cleavage. The relative decrease in counted fluorescent punctate particles before and after TEV protease treatment. The signal drops indicate MscL-GFP in HSLBs was easily accessible (oriented away from the substrate).

To make our expression platform more widely applicable, we decided to investigate the co-translational insertion of MscL-GFP into a preformed HSLB. The vesicle fusion method is typically limited to hydrophilic substrates, like glass, so enabling proteins to be synthesized after HSLB formation would unlock more diverse substrates where bilayer formation proceeds in other ways. Unlike synthesis into a vesicle, a potential complication of this strategy is that the nascent peptide chain may interact with the supporting surface and prevent protein expression or folding due to the proximity of the surface. To explore this, we first formed hybrid supported lipid bilayers containing the same range of lipid-to-diblock copolymer ratios as in our first approach, and then synthesized MscL-GFP directly into the HSLB. Bilayers were formed from protein-free vesicles, and excess vesicles were rinsed away before adding the cell-free reaction mixture above the adsorbed bilayer. We let the reaction proceed over the HSLB, allowing proteins to insert and fold into the supported membrane as they were synthesized, as depicted in FIG. 2A. Reaction times were determined empirically by monitoring GFP fluorescence over time. We allowed the reaction to proceed to a point where we could discriminate individual fluorescence points using TIRF microscopy, and then rinsed away unreacted materials to stop the reaction.

After protein was expressed into preformed supported bilayers containing increasing amounts of diblock copolymer, we found that each HSLB composition provides punctate fluorescence spots, indicating that protein expression and insertion is occurring directly into the supported bilayers (FIG. 7). After determining the number of particles for each sample, we added TEV protease and let the enzyme cleave the exposed GFP molecules from the membrane bound MscL region. We then rinsed each of the samples to remove cleaved GFP and imaged each sample again, as shown for 25 mol % diblock copolymer in FIG. 2B. Each composition tested can be seen in FIG. 7. After counting individual proteins left after the protease treatment and comparing them to the initial protein counts, we observed again that nearly all GFP is cleaved, as quantified in FIG. 2C. As with approach 1, this result indicates that essentially all the protein inserted into the membrane is oriented uniformly and unidirectionally away from the support. But comparing the two approaches, co-translation of protein into a preformed HSLB leads to slightly better protein orientation, about 95% versus 90%. HSLBs with 50 mol % diblock copolymer have slightly more GFP fluorescence relative to compositions with less diblock copolymer, which we hypothesize is due to some steric hindrance from the high percentage of diblock copolymer slightly blocking access by TEV protease. This second approach is further versatile because this protein expression and integration approach can potentially be used with HSLBs formed by any means (beyond vesicle fusion, e.g., Langmuir-Blodgett, SALB, etc.) making this technique advantageous for coating surfaces with lipid compositions incompatible with vesicle fusion, but requiring the presentation of proteins in a membrane environment (Jackman et al., Langmuir 2020, 36, 1387-1400; Su et al., ACS Appl. Bio Mater. 2019, 11, 43799-73810).

Diblock Copolymers Enhance the Mobility of Co-Translationally Inserted Membrane Proteins in HSLBS.

Once we incorporated MscL-GFP into HSLBs and identified the orientation, we investigated whether the HSLB could maintain protein mobility using single particle tracking techniques. Conveniently, the GFP tag on the protein can be used to track its movement in the HSLB over time, which enabled us to quantify mobility by calculating diffusion coefficients and mobile fractions. We analyzed protein motion for both protein incorporation approaches and observed similar results.

Figure 3:
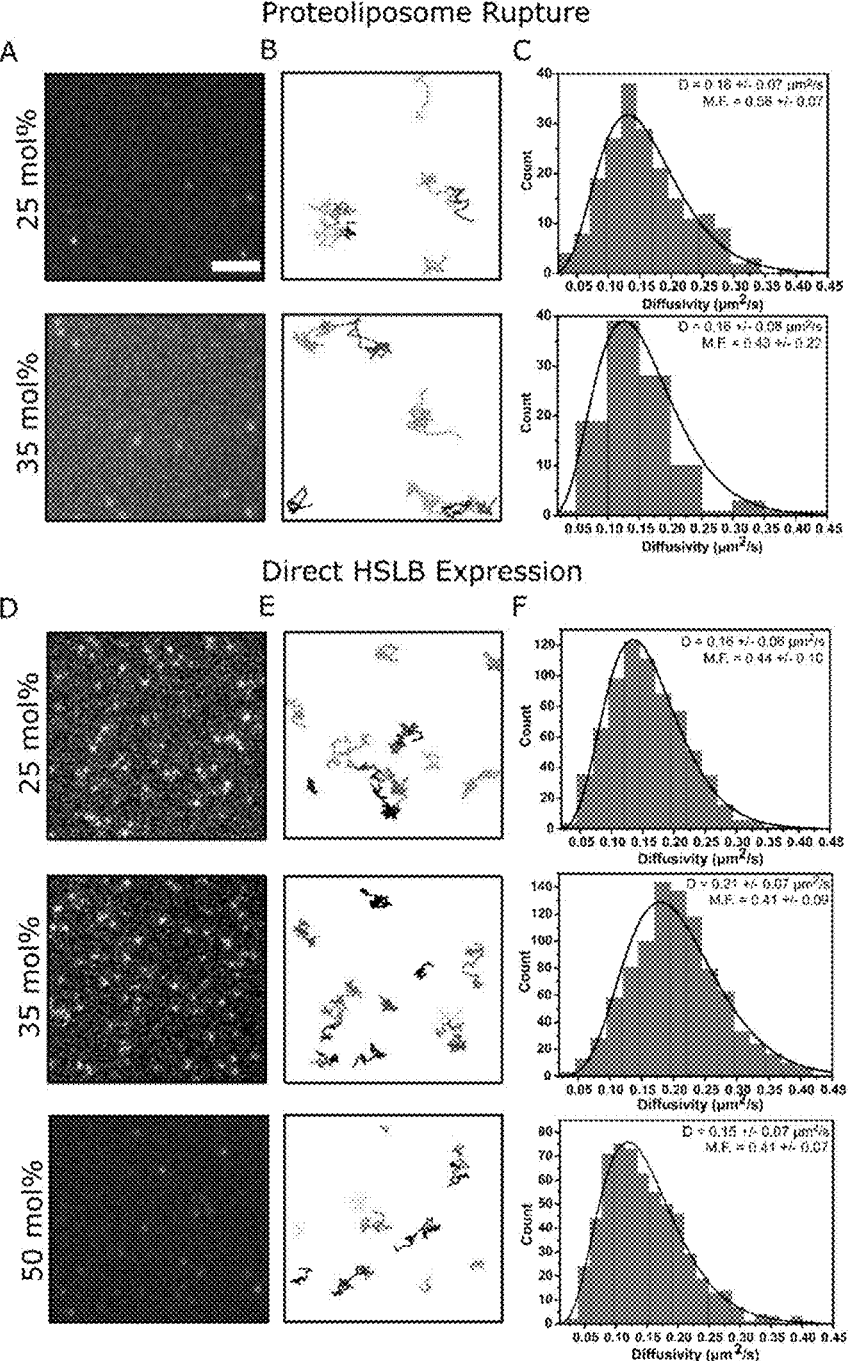
FIG. 3 shows MscL-GFP proteins tracked in HSLBs containing 25 mol % PEO-b-PBD and 35 mol % PEO-b-PBD formed by protein expression into hybrid vesicles or 25-50 mol % PEO-b-PBD formed by direct insertion into a preformed HSLB. (A) Representative TIRF image of MscL-GFP in HSLB. (B) Representative trajectories of MscL-GFP diffusion in the HSLB. (C) Diffusion coefficient histograms for MscL-GFP tracking experiments along with calculated diffusivities and mobile fraction. (E-H) Corresponding figures for direct HSLB expression. (scale bar 5 um).

We observed no protein mobility in 0% diblock copolymer. Similarly, 15 mol % diblock copolymer resulted in only one or two single proteins exhibiting any motion. However, at 25 and 35 mol % diblock copolymer concentrations, a significant number of proteins were mobile in the HSLB formed by the vesicle fusion method. The direct expression into preformed HSLBs also resulted in mobile proteins at 25 and 35 mol % diblock copolymer, but also in 50 mol %. Representative images of expressed, diffusive proteins and trajectories are shown in FIG. 3A-B for the vesicle-based reaction and FIG. 3D-E for the direct expression into the HSLB. We collected the trajectories of individual MscL-GFP molecules and plotted mean square displacements (MSD) as a function of time to determine diffusion coefficients and protein confinement. For normal diffusion, the MSD plot as a function of time gives a straight line with the slope proportional to the diffusion coefficient. We observed curved plots, which indicates possible confinement effects due to the diblock copolymer in these HSLBs. Therefore, we used the initial slope of the first three time points to determine the local homogenous diffusion constant (Liu et al., Langmuir 2018, 34 (3), 1061-1072; Richards et al., Langmuir 2016, 32 (12), 2963-2974; Kusumi et al., Biophys. J. 1993, 65 (5), 2021-2040; Smith et al., Biophys. J. 1999, 76 (6), 3331-3344). Representative MSD measurements over time for all compositions with mobile proteins are shown in FIG. 8.

By performing single particle tracking analysis we were able to calculate the mobile fraction and mean square displacement (MSD) and fit a gamma distribution to identify the average diffusivity of mobile proteins in HSLBs as seen in FIGS. 3C and 10. The calculated diffusivity of mobile MscL-GFP molecules in the 25% and 35% diblock copolymer HSLBs is $0.16\pm0.07$ $\mu m^2/s$ and $0.16\pm0.08$ $\mu m^2/s$ for Approach #1, and $0.16\pm0.06$ $\mu m^2/s$ and $0.21\pm0.07$ $\mu m^2/s$ from Approach #2, respectively. The 50 mol % diblock copolymer formed by direct expression has proteins with a diffusivity of $0.15\pm0.07$ $\mu m^2/s$. The mobile fraction in each sample is roughly 0.4-0.6. This indicates that both approaches of incorporating proteins into HSLBs provide a nearly identical HSLB with mobile transmembrane proteins directly integrated using CFPS. Either direct translation into a HSLB or the vesicle fusion using 25 mol % to 35 mol % diblock copolymer, or direct expression using 50 mol %, provides a membrane with unidirectional orientation and protein mobility. The benefit of the diblock copolymer is potentially explained by the hydrophilic PEO units in the diblock copolymer provide cushioning from the glass surface, which presumably prevents interaction and denaturation of MscL-GFP against the glass support, as is observed in the lack of protein mobility in the DOPC-only SLB (de Gennes, Scaling Concepts in Polymer Physics; Cornell University Press: Ithaca, NY, 1979).

The protein diffusivity we observed is lower than has been previously reported for similar sized membrane proteins in SLBs that were formed by more traditional methods involving protein reconstitution or native cellular material (Liu et al., Langmuir 2018, 34 (3), 1061-1072; Richards et al., Langmuir 2016, 32 (12), 2963-2974; Kawate et al., Nature 2009, 460 (7255), 592-598). However, we included diblock copolymers in our HSLBs and we observed that the lipid diffusivity was reduced at 25 and 35 mol % diblock copolymer to around ~0.3 ($\mu m^2/s$) and that the lipids were not mobile in 50 mol %. The increased viscosity from the diblock copolymer can explain a reduction in protein mobility, as we observed a decrease in lipid mobility down to zero as the amount of diblock copolymer was increased (FIGS. 9 and 10) which is consistent with previous studies (Gettel et al., J. Am. Chem. Soc. 2014, 136 (29), 8-11). Despite this decrease in lipid diffusion, we observed that over 40% of the proteins were mobile above a certain amount of diblock copolymer. Since the hydrophilic PEO region of the diblock copolymer is only expected to extend maximally to 2 nm (de Gennes, Scaling Concepts in Polymer Physics; Cornell University Press: Ithaca, NY, 1979), it is possible that some proteins may still interact with the support, causing some of the proteins to remain immobile. Longer hydrophilic regions may help reduce this interaction to increase diffusivity and provide a larger mobile fraction, but there is a tradeoff: longer chain polymersomes are harder to rupture into HSLBs and they may decrease protein insertion as the hydrophilic chain length increases.

Hybrid Supported Lipid Bilayers (SLBs) have Two-Dimensional Fluidity

Two-dimensional fluidity of lipids and membrane constituents is an important cellular property that must be maintained in the SLB for many applications as it enables the co-planar interaction of biomolecules, a fundamental process that is required for proper biological activity. We used liposome fusion methods to form SLBs on hydrophilic glass surfaces and fluorescence recovery after photobleaching (FRAP) methods to monitor the lipid fluidity. We conducted FRAP experiments on HSLBs containing a range of lipid to diblock copolymer ratio (0 mol % to 100 mol % PEO-b-PBD) with ~1 mol % of TR-DHPE, a fluorescently labelled phospholipid. Our results indicated that upon photobleaching, HSLBs with 0, 15, 25 and 35 mol % of diblock copolymer recovered fluorescence signals in the photobleached region completely over time, whereas HLSBS containing 50 mol % or 100 mol % diblock copolymer did not recover. In FIG. 9A-B, we have shown a schematic representation of HSLBs containing 0, 15 and 50 mol % diblock copolymer and corresponding FRAP images with time. A scan line across the photobleaching spot was drawn for each image to measure the trend of fluorescence recovery with time in this region (FIG. 10). Using these recovery profiles, we calculated the diffusion coefficient (D) of lipid molecules in HSLBs and their corresponding lipid mobile fraction (Table 1). In the membranes that do exhibit mobility, the overall lipid mobile fraction, however, remains close to that of SLBs consisting of pure DOPC. These observations indicate that DOPC liposomes containing 0, 15, 25 and 35 mol % diblock copolymer can form diffuse fluid SLBs/HSLBs on a glass surface, whereas 50 and 100 mol % copolymer containing liposomes are unable to do so.

There are two possible reasons why the diffusion coefficient decreases as the mole percent of diblock copolymer increases. One possibility is that increasing the concentration of diblock copolymer increases the viscosity of the membrane (Jacobs et al., Proc. Natl. Acad. Sci. U.S.A 2019, 116 (10), 4031-4036), and as such, the diffusion coefficient decreases. A second possibility is that increasing the amount of diblock copolymer results in more rigid vesicles (Bermúdez et al., Langmuir 2004, 20 (3), 540-543) that do not readily rupture to form a bilayer, and thus there are obstacles or defects in the layer that constrain the diffusive motion. We can rule out this latter possibility by looking at the trend in mobile fraction. For all formulations that are mobile, the mobile fractions are 95% or better. If there was a significant number of unruptured vesicles, the mobile fraction would also decrease, but the relative consistency across the compositions instead points to increasing viscosity as the reason for the decreasing diffusion.

According to previous studies, diblock copolymers can entangle or interact with hydrophilic surfaces (Goertz et al., *ACS Nano* 2012, 6 (2), 1532-1540) which increases the viscosity of the HSLB membrane and then decreases the diffusivity of the lipid molecules. This data tells us that we can tune the mobility by modulating viscosity through diblock copolymer composition. The observed trends in lipid diffusivity are in good agreement with other lipid and block diblock copolymer SLBs (Gettel et al., J. Am. Chem. Soc. 2014, 136 (29), 8-11; Paxton et al., Soft Matter 2018, 14 (40), 8112-8118).

TABLE 1

Diffusivity and Mobile Fraction of TR-DHPE in DOPC and PEO-b-PBD Containing Supported Lipid Bilayer on Glass

| mol % PEO-b-PBD | Diffusion Coefficient D ($\mu m^2/s$) | Mobile Fraction (M.F) |
|---|---|---|
| 0 | 1.01 ± 0.16 | 0.96 ± 0.05 |
| 15 | 0.54 ± 0.06 | 0.96 ± 0.04 |
| 25 | 0.31 ± 0.05 | 1.00 + 0.02 |
| 35 | 0.17 ± 0.06 | 0.90 ± 0.05 |
| 50 | Immobile | N/A |
| 100 | Immobile | N/A |

Somewhat surprisingly, though lipid diffusion drops significantly with increasing polymer content, we observed that proteins expressed directly into a preformed HSLB with 50 mol % diblock copolymer were mobile. We hypothesize that proteins expressed into hybrid membranes can exhibit local diffusion on the sub-micron scale even when there is not long-range lipid diffusivity over the micron scale. To answer this, we calculated a confinement radius of mobile proteins based on the max displacement of expressed MscL-GFP shown in FIG. 11. We calculate that HSLBs with 50 mol % diblock copolymer have a confinement radius nearly half that of 25 and 35 mol %. This result provides evidence that the HSLB is more restrictive yet still permits local protein motion while preventing overall lipid diffusivity at high diblock copolymer concentrations.

Incorporation of Diblock Copolymer Creates HSLBs with Tunable Protein and Lipid Properties.

Figure 4:
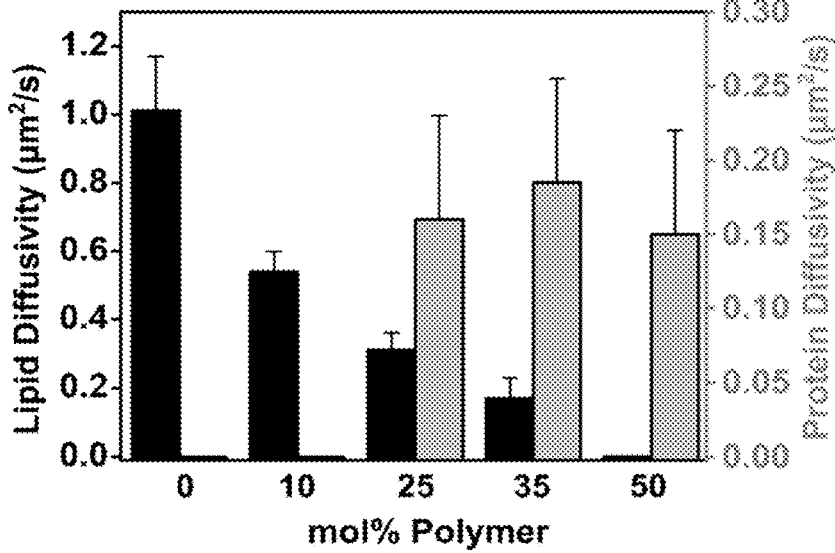
FIG. 4 shows the comparison of lipid and protein diffusivity from 0 mol % to 50 mol % diblock copolymer. The lipid diffusivity is a maximum at 0 mol % and then decreases with an increase in diblock copolymer concentration. Protein diffusivity is achieved in a minimum of 25 mol % diblock copolymer.

After analyzing protein and lipid mobility in HSLBs with varying concentrations of diblock copolymer, we can now compare the trends of each (FIG. 4). We found that lipid molecules in up to 35 mol % diblock copolymer containing HSLBs are mobile with nearly full recovery of a bleached spot intensity, whereas for 50 mol % diblock copolymer containing HSLBs, the bleached spot intensity did not recover with time, indicating either a very low lipid diffusivity, or unruptured vesicles. We also conducted complementary quartz crystal microbalance with dissipation (QCM-D), shown in FIG. 12. These measurements suggest that a bilayer does form at 50 mol % diblock copolymer, so we attribute the lack of recovery of bleaching spot intensity in the FRAP measurements to the low diffusion coefficient from a highly viscous HSLB. Since the presence of proteins may hinder vesicle rupture at this threshold composition, we attribute the lack of protein mobility from the vesicle fusion of 50 mol % diblock copolymer to unruptured vesicles. Overall, although the lipid diffusivity decreases, we observed that the mobile fraction remains high with an increase in diblock copolymer.

We monitored the QCM-D response of hybrid liposomes with increasing mol percentage of diblock copolymer to assess bilayer formation. The addition of hybrid vesicles with 15 mol % diblock copolymers also exhibits a typical SLB QCM-D response shape, like DOPC. But here we see the kinetics of bilayer formation is apparently a two-step process, with a faster regime initially at the transition point, which then switches over to a slower rise until reaching the final plateau. The two kinetic regimes are mirrored in the dissipation signal as well. These two regimes could result from some vesicles fusing with a more DOPC-like pattern of adsorption then rupture, and those fusing with a slower kinetics that are clearly influenced by the diblock copolymer presence. At the plateaus, the overall mass is what we would expect: a shift in frequency due to the diblock copolymer weight, and a shift in dissipation aligning with greater diblock copolymer energy absorption (FIG. 12).

With a further increase in diblock copolymer percentage in DOPC vesicles, a distinct change in QCM-D response is noticed. In 25 mol % diblock copolymer hybrid vesicles, there is initially a sharp decrease followed by a slight increase in frequency, whereas with 35 and 50 mol % diblock copolymer, the sharp decrease is followed by an almost constant frequency. Similarly, in the dissipation profiles, a sharp increase in dissipation, followed by an almost constant value is observed. We notice that as the mol % of diblock copolymer is increased to 50% in increments of 10%, the change in frequency and dissipation follow regular monotonic increases of discrete amounts, seeming to correspond with the regular addition of mass of the diblock copolymer and its dissipative properties. As a point of reference, in 100 mol % diblock copolymer formulation, we found a rapid decrease in frequency and an increase in dissipation, but here the final values of frequency and dissipation were extreme, suggesting only vesicle adsorption on the silica surface with no rupture or bilayer formation (highest mass and highest dissipation). As such, we conclude that bilayers are forming as high as 50 mol % diblock copolymer.

The presence of incorporated protein also does not affect the lipid diffusivity (FIGS. 13 and 14). Importantly, HSLBs with at least 25 mol % diblock copolymer allow for protein diffusion while samples with 0 and 15 mol % do not.

This range of properties provides the ability to select for certain characteristics or reaction schemes depending on the system of interest. Proteins that may not insert efficiently into a flat membrane surface may benefit from the vesicle based method in the first approach, and membrane compositions that are not compatible with vesicle fusion may benefit from the second approach using direct expression. In terms of lipid mobility, certain studies may desire slower diffusion with a high mobile fraction to better regulate biological processes or even limit diffusion entirely to isolate effects without promoting phase separation. Incorporating diblock copolymers can achieve this without changing the underlying lipid composition. Furthermore, given that protein mobility is an important property for many membrane processes, being able to preserve this aspect in this platform with an easy way to incorporate proteins should open the door to many exciting applications of this cell-free approach of creating a biomimetic proteinaceous membrane surfaces. Protein mobility is a key process that will enable this platform to be used to analyze complex biological functions. Binding assays with small molecules, proteins, antibodies, and viral particles among others often rely on multivalent interactions with membrane species that result from planar motion. Analyzing protein sub-unit oligomerization and channel formation is another important biological phenomenon dependent on membrane mobility. This could enable these HSLBs to be used with CFPS to study membrane protein function or used as an array for pathogen detection. Conversely, there are applications where reducing the lipid mobility can be useful. One example would be in creating arrays of proteins where each location is static and can be used as a test point, for example, in drug interactions and discovery. Such an approach to reduce diffusion via inclusion of diblock copolymers can easily create bio-mimetic platforms on a wide variety of surfaces without a need to use microfabrication to create barriers to protein motion.

An alternative hypothesis could be that proteins may not be inserted properly but rather be adsorbed on top of the membrane and diffusing there. We have two pieces of evidence to discount this possibility. First, the folding reporter should only fluoresce with proper folding, providing the support that the protein is inserted into the membrane correctly. Because we track proteins that are fluorescent, we are, by definition, tracking only those that are expected to be folded properly. In a second experiment, we sought to determine if the MscL protein was not only properly folded, but in its fully assembled, homopentamer state (Perozo et al., Nature 2002, 418, 942-948). To determine the MscL oligomeric state, we used single-molecule bleach step analysis to count the number of subunits of the protein complexes in the field of view for 25% diblock copolymer HSLBs. Subunit counting relies on the detection of the individual bleach steps of fluorescently tagged proteins-of-interest (Singh et al., Sci. Rep. 2020, 10, No. 14866; Ulbrich et al., Nat. Methods 2007, 4, 319-321). For oligomeric protein complexes such as MscL, if all of the fluorescently tagged subunits were fluorescent, the number of photo-bleaching steps would be equal to the number of subunits per protein complex. However, fluorescent proteins such as GFP can improperly fold and be nonfluorescent, reducing the number of bleach steps observed. Although the fraction of misfolded dark proteins can vary with conditions, it is typically ~20-25% of the total. By assuming a value for the fluorescent fraction (77% of our data), the bleach step histogram can be corrected for "missed" subunits (Singh et al., Sci. Rep. 2020, 10, No. 14866). Our corrected bleach step histogram shows that a number of MscL-GFP protein complexes in the bilayer displayed five discrete bleaching steps (FIG. 16). Although we did observe populations of smaller oligomers, with tetramers being the largest fraction, this is typically seen due to bleach steps occurring too close in time to accurately separate and to bleaching that can occur during focusing and locating the field of view. Based on these results, we believe that the majority of cell-free synthesized MscL-GFPs oligomerize as pentamers in our system, validating the applicability for conducting single-molecule studies. Thus, we can conclude that the proteins we observe in the HSLBs made with moderate amounts of diblock copolymer are folded, inserted, in a native pentameric form, and able to diffuse within an apparently confined bilayer environment.

Conclusion:

Here, we showed that planar, supported bilayers could be assembled from phospholipids and diblock copolymers and that mobile, oriented membrane proteins could be integrated using cell free synthesis methods. We demonstrated that a GFP-labelled ion channel, MscL-GFP, could be incorporated into HSLBs by two different approaches: (1) We first expressed MscL-GFP into liposomes, and showed using a protease cleavage assay that proteoliposomes can form HSLBs and maintain the orientation of integrated MscL-GFP after rupture and (2) We showed that MscL-GFP could be integrated into HSLBs after formation by incubating a cell-free reaction with the pre-formed HSLBs. Our findings indicate that CFPS provides a potentially powerful strategy to assemble planar lipid platforms with mobile, oriented biological proteins.

A critical finding of this study is that the inclusion of small amounts of a diblock copolymer into HSLBs facilitated the mobility of the integrated membrane proteins. The lack of protein mobility in lipid bilayers has been an important obstacle preventing the full potential of SLBs in both biophysical and technological applications (Diaz et al., Langmuir 2008, 24 (13), 6820-6826; Goennenwein et al., Biophys. J. 2003, 85 (1), 646-655). Previous attempts to circumvent this issue have used polymer layers to elevate the height of the bilayer, prevent non-specific interactions of the protein with the SLB substrate, and enable mobility. Yet, these approaches either offer unilateral benefits or complicated formation techniques. As we demonstrated, diblock copolymers can readily rupture into HSLBs with tunable properties and have been shown to improve the mechanical properties of lipid membranes (Bermudez et al., Macromolecules 2002, 35 (21), 8203-8208), which could be beneficial in surfaces requiring long-term stability.

As biotechnology turns towards integrating biotic and abiotic surfaces, such as the development of biosensors for protein activity, therapeutic screening, or pathogen detection, many promising applications of SLBs using transmembrane protein-based model membranes are hindered due to limited methods to insert oriented, mobile membrane proteins into SLBs. The ability to synthesize proteins directly into a supported membrane without the need for cell culture or protein purification provides a powerful tool in biotechnology applications. We have demonstrated, for the first time, the utilization of HSLBs constructed from phospholipids and diblock copolymers with transmembrane proteins that mimic native biological behavior. This approach is expected to be compatible with various SLB fabrication methods, opening this new way to incorporate membrane proteins into tunable SLBs using cell free expression methods. We anticipate that the combination of CFPS and hybrid SLB platforms to integrate membrane proteins in model membranes will provide a wide breadth of interesting uses in biophysical studies and technological applications. Because of the easily tunable properties and the maintenance of native biological features, in the future, cell-free membrane protein functionalized SLB platforms can be used to address a number of central challenges such as membrane transport phenomena, membrane protein biosensors, screening of therapeutically relevant membrane proteins, or complex binding events from a range of targets, on nearly any surface.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Other embodiments are within the following numbered paragraphs.

1. A hybrid supported lipid bilayer (HSLB) comprising:
a phospholipid;
a copolymer; and
a membrane protein,
wherein the membrane protein is functional, properly oriented within the lipid bilayer, and mobile within the lipid bilayer.
2. The HSLB of paragraph 1, wherein the phospholipids comprise one or more phospholipids selected from the group consisting of 1,2-dioleoyl-sn-glycero-3-phosphocholine (DOPC) and poly(ethylene oxide)-b-polybutadiene (PEO$_{14}$-b-PBD$_{22}$).
3. The HSLB of paragraph 1, wherein the copolymer comprises a diblock copolymer.
4. The HSLB of paragraph 1, wherein the copolymer comprises poly(ethylene oxide)-b-poly(butadiene) (PEO-b-PBD).
5. The HSLB of paragraph 1, wherein the HSLB comprises at least 25, 30, 35, 40, 45, or 50 mol % of copolymer.
6. The HSLB of paragraph 1, wherein the HSLB comprises between 25-35 mol % of copolymer.
7. The HSLB of paragraph 1, wherein the membrane protein comprises an integral membrane protein.
8. The HSLB of paragraph 1, wherein the membrane protein comprises mechanosensitive channel of large conductance (MscL).
9. The HSLB of paragraph 1, wherein the membrane protein is properly oriented within the lipid bilayer when it is oriented in a native physiological orientation.
10. The HSLB of paragraph 1, wherein the HSLB comprises a plurality of copies of the membrane protein and wherein at least 90% of the plurality of copies of the membrane protein have a native physiological orientation.
11. The HSLB of paragraph 1, wherein the HSLB comprises a plurality of copies of the membrane protein and wherein at least 95% of the plurality of copies of the membrane protein have a native physiological orientation.
12. A method of preparing HSLB of any one of paragraphs 1-11, the method comprising:
preparing a hybrid vesicle comprising phospholipids and copolymers; and
expressing a membrane protein with a cell-free expression system, wherein the membrane protein is co-translationally inserted into the hybrid vesicle; and
fusing the hybrid vesicle to form a HSLB.
13. A method of preparing the HSLB of any one of paragraphs 1-11, the method comprising):
forming a HSLB comprising a phospholipid and a copolymer; and
expressing a membrane protein with a cell-free expression system, wherein the membrane protein is co-translationally inserted into the HSLB.
Other embodiments are within the claims.

What is claimed is:
1. A hybrid supported lipid bilayer (HSLB) comprising:
a solid surface;
a lipid bilayer supported on the solid surface, the lipid bilayer comprising a phospholipid and a copolymer, wherein the copolymer is present in the lipid bilayer in an amount of 15 mol. % to 50 mol. % relative to a combined amount of the phospholipid and the copolymer; and
a plurality of copies of a membrane protein, wherein:
the plurality of copies of the membrane protein is functional, properly oriented within the lipid bilayer, and mobile within the lipid bilayer; and
at least 82% of the plurality of copies of the membrane protein have a native physiological orientation relative to the solid surface;
wherein at least one of condition (I) and condition (II) is satisfied:
(I) the HSLB has a membrane protein mobile fraction of at least 0.4; and
(II) the HSLB has a membrane protein diffusivity in a range of 0.08 μm$^2$/s to 0.28 μm$^2$/s.

2. The HSLB of claim 1, wherein the phospholipid comprises one or more phospholipids selected from the group consisting of 1,2-dioleoyl-sn-glycero-3-phosphocholine (DOPC) and poly(ethylene oxide)-b-polybutadiene ($PEO_{14}$-b-$PBD_{22}$).

3. The HSLB of claim 1, wherein the copolymer comprises a diblock copolymer.

4. The HSLB of claim 1, wherein the copolymer comprises poly(ethylene oxide)-b-poly(butadiene) (PEO-b-PBD).

5. The HSLB of claim 1, wherein the copolymer is present in the lipid bilayer in an amount of 25 mol. % to 50 mol. % relative to a combined amount of the phospholipid and the copolymer.

6. The HSLB of claim 1, wherein the copolymer is present in the lipid bilayer in an amount of 25 mol. % to 35 mol. % relative to a combined amount of the phospholipid and the copolymer.

7. The HSLB of claim 1, wherein the membrane protein comprises an integral membrane protein.

8. The HSLB of claim 1, wherein the membrane protein comprises mechanosensitive channel of large conductance (MscL).

9. The HSLB of claim 1, wherein the membrane protein is properly oriented within the lipid bilayer when it is oriented in a native physiological orientation.

10. The HSLB of claim 1, wherein the HSLB comprises a plurality of copies of the membrane protein and wherein at least 90% of the plurality of copies of the membrane protein have a native physiological orientation.

11. The HSLB of claim 1, wherein the HSLB comprises a plurality of copies of the membrane protein and wherein at least 95% of the plurality of copies of the membrane protein have a native physiological orientation.

12. A method of preparing the HSLB of claim 1, the method comprising:

preparing a hybrid vesicle comprising phospholipids and copolymers; and expressing a membrane protein with a cell-free expression system, wherein the membrane protein is co-translationally inserted into the hybrid vesicle; and rupturing the hybrid vesicle on a solid surface to form the HSLB.

13. A method of preparing the HSLB of claim 1, the method comprising:

forming a lipid bilayer supported on a solid surface, the lipid bilayer comprising a phospholipid and a copolymer; and expressing a membrane protein with a cell-free expression system, wherein the membrane protein is co-translationally inserted into the lipid bilayer to form the HSLB.

14. The HSLB of claim 1, wherein the solid surface is a glass slide.

15. The HSLB of claim 1, wherein the condition (I) is satisfied such that the HSLB has a membrane protein mobile fraction of at least 0.4.

16. The HSLB of claim 15, wherein the HSLB has a lipid mobile fraction of at least 0.85.

17. The HSLB of claim 15, wherein the copolymer is present in the lipid bilayer in an amount of 25 mol. % to 50 mol. % relative to a combined amount of the phospholipid and the copolymer.

18. The HSLB of claim 1, wherein the condition (II) is satisfied such that the HSLB has a membrane protein diffusivity in a range of 0.08 $\mu m^2$/s to 0.28 $\mu m^2$.

19. The HSLB of claim 18, wherein the HSLB has a lipid diffusivity in a range of 0.11 $\mu m^2$/s to 0.60 $\mu m^2$/s.

20. The HSLB of claim 18, wherein the copolymer is present in the lipid bilayer in an amount of 25 mol. % to 50 mol. % relative to a combined amount of the phospholipid and the copolymer.

\* \* \* \* \*